United States Patent
Yang et al.

(10) Patent No.: US 10,376,155 B2
(45) Date of Patent: Aug. 13, 2019

(54) METHOD AND SYSTEM FOR GENERATING PHYSIOLOGICAL SIGNALS WITH FABRIC CAPACITIVE SENSORS

(71) Applicants: Chang-Ming Yang, Miaoli (TW); Tzulin Yang, Taipei (TW); Ching Wen Yang, Taipei (TW); Hao Yang, Taipei (TW)

(72) Inventors: Chang-Ming Yang, Miaoli (TW); Tzulin Yang, Taipei (TW); Ching Wen Yang, Taipei (TW); Hao Yang, Taipei (TW)

( * ) Notice: Subject to any disclaimer, the term of this patent is extended or adjusted under 35 U.S.C. 154(b) by 752 days.

(21) Appl. No.: 13/671,345

(22) Filed: Nov. 7, 2012

(65) Prior Publication Data

US 2013/0066168 A1      Mar. 14, 2013

Related U.S. Application Data

(63) Continuation-in-part of application No. PCT/CN2010/001931, filed on Nov. 30, 2010, which
(Continued)

(51) Int. Cl.
  *A61B 5/01*      (2006.01)
  *A61B 5/0205*   (2006.01)
(Continued)

(52) U.S. Cl.
  CPC .............. *A61B 5/0205* (2013.01); *A61B 5/01* (2013.01); *A61B 5/0245* (2013.01);
(Continued)

(58) Field of Classification Search
  CPC ......... A61B 5/0205; A61B 5/443; A61B 5/05; A61B 5/4815; A61B 5/1121; A61B 5/01;
(Continued)

(56) References Cited

U.S. PATENT DOCUMENTS

| | | | |
|---|---|---|---|
| 1,168,132 A | 1/1916 | Wehner | |
| 6,210,771 B1 * | 4/2001 | Post | H05K 3/10 139/1 R |

(Continued)

FOREIGN PATENT DOCUMENTS

| | | |
|---|---|---|
| CN | 2641621 Y | 9/2004 |
| CN | 1718160 A | 1/2006 |

(Continued)

OTHER PUBLICATIONS

Rekimoto, Jun, "GestureWrist and GesturePad: Unobtrusive Wearable Interaction Devices"; Wearable Computers, 2001; Proceedings, Fifth International Symposium on Wearable Computers, IEEE 2001 (7 pages).

(Continued)

*Primary Examiner* — Rex R Holmes
(74) *Attorney, Agent, or Firm* — Chun-Ming Shih; HDLS IPR Services

(57) ABSTRACT

A system for generating physiological signals using a cloth capacitive sensor, includes a cloth, at least one conductive area arranged on the cloth, a signal circuit; a capacitive sensor formed between the cloth and a human body; a resistor R, a capacitor C, an inductor L, an operational amplifier, a diode, a Schmitt trigger, CMOS, a transistor, or an IC that forms a charge or discharge circuit, connected with the cloth capacitive sensor to change a signal range of frequency, cycle, voltage or current; wherein when a force, pressure, tensile force, torsion or tension is applied between the human body and the cloth, the capacitance changes, the circuit sends a signal, and the system receives the change in capacitance between the conductive cloth and the human body; wherein the change is represented by a frequency, cycle, voltage or current change.

25 Claims, 19 Drawing Sheets

Related U.S. Application Data is a continuation-in-part of application No. PCT/CN2010/000648, filed on May 7, 2010.

(51) Int. Cl.

| | | |
|---|---|---|
| *A61B 5/0245* | (2006.01) | |
| *A61B 5/11* | (2006.01) | |
| *G01L 1/14* | (2006.01) | |
| *A61B 5/0408* | (2006.01) | |
| *A61B 5/0478* | (2006.01) | |
| *A61B 5/0492* | (2006.01) | |
| *A61B 5/05* | (2006.01) | |
| *A61B 5/053* | (2006.01) | |
| *A61B 5/113* | (2006.01) | |
| *A61B 5/00* | (2006.01) | |
| *A61F 7/00* | (2006.01) | |
| *A61N 1/40* | (2006.01) | |
| *G01K 13/00* | (2006.01) | |

(52) U.S. Cl.
CPC .......... *A61B 5/0408* (2013.01); *A61B 5/0478* (2013.01); *A61B 5/0492* (2013.01); *A61B 5/05* (2013.01); *A61B 5/0537* (2013.01); *A61B 5/11* (2013.01); *A61B 5/112* (2013.01); *A61B 5/113* (2013.01); *A61B 5/1116* (2013.01); *A61B 5/1121* (2013.01); *A61B 5/443* (2013.01); *A61B 5/4809* (2013.01); *A61B 5/4815* (2013.01); *A61F 7/00* (2013.01); *A61N 1/40* (2013.01); *G01K 13/002* (2013.01); *G01L 1/146* (2013.01); *A61B 2562/0215* (2017.08)

(58) Field of Classification Search
CPC ... A61B 5/1116; A61B 5/0408; A61B 5/0478; A61B 5/0537; A61B 5/113; A61B 5/0492; G01K 13/002; A61F 7/00; A61N 1/40

See application file for complete search history.

(56) References Cited

U.S. PATENT DOCUMENTS

| | | | |
|---|---|---|---|
| 6,333,736 B1 * | 12/2001 | Sandbach | G06F 3/0414 178/18.03 |
| 6,469,524 B1 | 10/2002 | Oberdier | |
| 6,724,324 B1 | 4/2004 | Lambert | |
| 6,809,462 B2 | 10/2004 | Pelrine et al. | |
| 6,826,968 B2 | 12/2004 | Brantley et al. | |
| 7,135,983 B2 | 11/2006 | Filippov et al. | |
| 7,173,437 B2 | 2/2007 | Hervieux et al. | |
| 7,676,296 B2 | 3/2010 | Fujii et al. | |
| 8,298,968 B2 * | 10/2012 | Swallow | D03D 1/0088 345/173 |
| 2002/0151816 A1 | 10/2002 | Rich et al. | |
| 2005/0215915 A1 | 9/2005 | Noda et al. | |
| 2007/0248799 A1 * | 10/2007 | DeAngelis | G01L 1/146 428/209 |
| 2010/0170704 A1 | 7/2010 | Yang et al. | |
| 2011/0043225 A1 * | 2/2011 | Sullivan | A61B 5/04004 324/658 |
| 2011/0046518 A1 * | 2/2011 | Fischer | A61B 5/103 600/594 |
| 2012/0215076 A1 * | 8/2012 | Yang | A61B 5/0205 600/301 |

FOREIGN PATENT DOCUMENTS

| | | | |
|---|---|---|---|
| CN | 101622518 A | 1/2010 | |
| EP | 1674036 A1 * | 6/2006 | ......... A61B 5/04085 |
| JP | 2002-224051 A | 8/2002 | |
| JP | 2003-275185 A | 9/2003 | |
| JP | 2003-339652 A | 12/2003 | |
| JP | 2004-209003 A | 7/2004 | |
| JP | 2004-261542 A | 9/2004 | |
| JP | 2006-346093 A | 12/2006 | |
| JP | 2007-151661 A | 6/2007 | |
| WO | 2005/032368 A1 | 4/2005 | |
| WO | 2007/033520 A1 | 3/2007 | |
| WO | 2009-030067 A1 | 3/2009 | |
| WO | 2009/033361 A1 | 3/2009 | |
| WO | 2009/033362 A1 | 3/2009 | |
| WO | 2009/050702 A2 | 4/2009 | |
| WO | 2009-084387 A1 | 7/2009 | |

OTHER PUBLICATIONS

International Search Report dated Mar. 10, 2011, from the State Intellectual Property Office, The People's Republic of China, for related International Application No. PCT/CN2010/001931, with English translation (10 pages).

Notice of Reasons for Rejection ("Office Action") dated Nov. 18, 2014 by the Japan Patent Office in corresponding Japanese Patent Application No. JP 2013-508345, with partial Google machine-translation (9 pages).

Tae-Ho Kang, et al, "Sensors on Textile Substrate for Home-Based Healthcare Monitoring", Proceedings of the 1st Distributed Diagnosis and Home Healthcare (D2H2) Conference, Arlington, VA, Apr. 2-4, 2006 (3 pages).

Cliff Randell,et al,"The Sensor Sleeve: Sensing Affective Gestures", Ninth International Symposium on Wearable Computers; Workshop on On-Body Sensing, Oct. 2005 (5 pages).

J. Meyer, et al, "Textile Pressure Sensor for Muscle Activity and Motion Detection", the 10th IEEE International Symposium on Wearable Computers, Nov. 2006 (4 pages).

* cited by examiner

< Vcv and Vo >

METHOD AND SYSTEM FOR GENERATING PHYSIOLOGICAL SIGNALS WITH FABRIC CAPACITIVE SENSORS

This is a Continuation-in-Part application of PCT/CN2010/001931, filed on Nov 30, 2010, which claims priority of PCT/CN2010/000648, filed on May. 7, 2010. Both PCT/CN2010/001931 and PCT/CN2010/000648 have expired. This application claims the benefits of these prior application and incorporates these prior application by reference in their entirety.

TECHNICAL FIELD

The invention relates to a method and system capable of sensing physiological functions of human body, such as that in physical training, medical treatment, fitness and health care, in particular to a method and system, wherein at least one piece of cloth where at least a conductive area is arranged to be contacted with human body. Capacitance is formed between the cloth and human body. As pressure, pull or strain exists between the human body and the cloth, the capacitance changes, or the dielectric constant there between is changed so that when the capacitance changes, a resonance frequency, a voltage or a current is generated under the effect of a signal provided externally. And the resonance frequencies, voltages or currents are used to sense the physiological parameters of the human body, such as breath, swallowing, humidity, coughing, sweating, and heartbeat, as well as posture parameters such as position, speed, acceleration, angle, angular speed, and angular acceleration. And the capacitive sensor itself further can be served as a sensor to sense the pressure, pull and tension of the human body or served as a displacement sensor of the human body that generates distinguishable signals.

BACKGROUND ART

Along with huge progress of living standard and health care service, life expectancy of human is prolonged gradually and proportion of aging population increases continuously. As for the ageing society, problems concerning social welfare, medical and pharmaceutical technologies and social security system appear and increasing aged people cannot be taken care of appropriately and adequately by their family members and their families. Therefore, sports, leisure, entertainment, etc. are among the necessary physiological monitoring items.

In order to sense the physiological signals of human body in a way that is free from foreign body sensation, a wearable sensor is the most important part. There has been technical discussion on this abroad. For example, Mr. Sergio used two conductive electrodes to sense pressure, based on a mechanism of providing a fixed frequency from an external system and sensing the capacitance between the two electrodes. The pressure changes are represented by voltage (see reference document 1). Another system used to sense breath is represented by distance changes: when a user breathes, the capacitance will change due to changes in the distances between the two electrodes (see reference document 2). Furthermore, the capacitance between the two conductive electrodes has been used to sense humidity (see reference document 3). Jun Rekimoto developed a technology capable of measuring the distance between conductive objects. He measured the capacitance between the electrodes and the conductive objects and used a transmitter and an electrode receiver. When human body approaches the two electrodes, the capacitance increases for sensing the proximity and position (proximity and position sensor). As the sensing gesture is not directly contacted with skin, equivalent parasitic capacitance is not taken into consideration. No different results are caused by different pressures, pull, or strain. In the text, watch form is adopted and a capacitance corresponds to a fox n of hand. When people sit on cloth, a shield layer is grounded, and the output end is represented by amplitude of voltage and its emitting signal is fixed and not oscillating. That is to say, it is invariable. (See reference document 4). Cliff Randell studied the situation that two pieces of conductive cloth form a capacitance, and when the posture of human body changes under the effect of external pressure, the capacitance changes along with the human body in his paper (see reference document 5). In Jan Meyer's study, his theory is as same as above ones, but material between the two pieces of conductive cloth is changed (see reference document 6). Finally, in Jingyuan Cheng's study, human body is served as a medium and conductive cloth is placed at both sides of the body to form a capacitance and a circuit is employed to measure the change of capacitance. In his study, he expresses to us that breathing and drinking water can generate different distinguishable signals (see reference documents 7).

In U.S. patent Ser. No. 11/68,132P, two pieces of cloth are used to measure the physiological change of human body, but the measured parameter is voltage change by means of change in capacitance between the conductive cloth due to change of human body.

In U.S. Pat. No. 6,826,968, a medium is placed between electrodes in row and line to form capacitance to measure the pressure, which measures the change of voltage by means of the change of capacitance between the two pieces of cloth along with pressure with a fixed frequency.

In U.S. Pat. No. 6,469,524, a signal is emitted to the first electrode, and the second electrode and the first electrode form a capacitance. When people approaches, the capacitance changes and meanwhile a phase shifted signal is generated.

In patent PCT/CN2008/001571, the conductive areas at both sides of the crack change along with external force which is irrespective of contact with human body.

In US patent 2005/0215915, two electrodes are pressed to cause distance change and change in capacitance. While in the invention, change in capacitance is generated along with pressure change between the body and the electrodes or dielectric constant change between the body and the electrodes.

In patent CN2641621, two conductive materials, such as metal sheets or fiber, generate change in capacitance under effect of pressure, which is irrespective of the body of testee. And insulating materials are required between the two electrodes.

In patent CN101622518A, change in capacitance is generated by pressure and shear force on the capacitive sensor while the capacitance between non-conductive material and human body is changed due to external force.

In patent CN1718160, the static capacitance used for measuring breath further utilizes change in capacitance of two conductive materials under pressure.

In patent JP2003339652A, heartbeat and breath sensor are obtained by the change in capacitance of the two electrodes under effect of pressure.

U.S. Pat. No. 6,724,324 is capacitive proximity sensor, which includes a first electrode that receives an AC signal, a second electrode that generates an input signal. The sensor further includes an intermediate electrode placed between the first and second electrodes and a grounded end for sensing whether the finger approaches the position or not.

U.S. Pat. No. 7,676,296 provides symmetrically arranged electrodes relative to the head of the main body, which include at least a first electrode and a second electrode. The first and second electrodes are selectively coupled at an AC voltage source for sensing the posture of the head of passengers in the vehicle. The electrodes are not contacted with the testee.

In US Patent 2007/00849341, an oscillator generates a signal to measure the resistance and capacitance of characters on cloth and paper. In the invention, an oscillator, in particular an unstable state oscillator is used to measure the change in capacitance between the electrodes of the cloth and the human body. The change in capacitance is represented by resonance frequency. For example, different physiological statuses induce interaction between the electrodes of the cloth and the human body so as to generate different resonance frequencies, voltages or currents which will change continuously along with the change on human body. Different physiological statuses generate different frequency, voltage or current change curves.

U.S. Pat. No. 7,173,437 uses a capacitive sensor to measure the biopotential. However, the invention measures the resonance frequency caused by interaction between the electrodes of the cloth and the human body. The invention measures the "change" generated by "Activity" of human body.

In U.S. Pat. No. 7,135,983, an oscillating circuit is used. When people approaches the electrodes, on and off capacitances are different. Therefore, the frequencies measured by the oscillating circuit are different. But this patent is used to measure on or off capacitance and there is only one electrode. However, the invention relates to the change in capacitance between the electrodes and the human body, which is the physiological change of human body but not only on or off capacitances. The invention reads the physiological signals under long time interaction of the electrodes of cloth and the human body. In U.S. Pat. No. 7,135,983, a single electrode is used and grounded virtually so that the change in capacitance is small. Due to the parasitic capacitance of human body, the accuracy and reliability are unstable. But in the invention, a loop is formed between the two electrodes and the human body. The physiological changes of human body such as hand movement, breathing, swallowing, coughing and etc change remarkably. And for different physiological changes, the frequency, voltage or current changes are different in characteristics. Therefore, the physiological changes of the human body can be judged by means of characteristics of the frequency, voltage or current changes. That is to say, the invention measures the continuous change between the human body and the electrodes and analyzes the change of characteristics of frequency, voltage or current in continuous change but not only on or off capacitances.

Thus it can be seen that in above cited prior art, change on amplitude of voltage or frequency signal is not remarkable. Therefore, the invention improves the prior art and designs an oscillator to generate frequency and is provided with at least one piece of conductive cloth which is contacted with the human body to form capacitance. When the human body has physiological changes, the capacitance changes therewith. Therefore, the invention can sense the change of resonance frequency. The signal is remarkable and easy to judge.

The physiological signals measured by the invention are obtained by using wearable conductive cloth, in particular to sense breathing, swallowing, coughing, posture, humidity and pressure degree of each part of the human body to generate distinguishable signals. Specifically, when the capacitive sensors are in different positions, the capacitances of the capacitive sensors are different so that the voltage, current or frequency ranges measured are different so as to obtain the physiological signals at different positions.

Reference document 1. M. Sergio, et al, A Textile-Based Capacitive Pressure Sensor, Sensor Letters, Volume 2, Number 2, Jun. 2004, pp. 153-160(8).

Reference document 2. Tae-Ho Kang, et al, Sensors on Textile Substrate for Home-Based Healthcare Monitoring, Proceedings of the 1st Distributed. Diagnosis and Home Healthcare (D2H2) Conference.

Reference document 3. F. Di Francesco, D. Costanzo, P. Salvo, D. De Rossi Towards the measurement of sweat rate via wearable sensors, 4th pHealth conference 2007.

Reference document 4. J. Rekimoto, ET AL, Gesture and Gesture Pad: Unobstrusive Wearable International Devices, Proceedings of the 5th IEEE International Symposium on Wearable Computers 2001.

Reference document 5. Cliff Randell, et al, The Sensor Sleeve: Sensing Affective Gestures. Ninth International Symposium on Wearable Computers—Workshop on On-Body Sensing. October 2005.

Reference document 6. J. Meyer, et al, Textile Pressure for Muscle Activity and Motion Detection, the 10th IEEE International Symposium on Wearable Computers, 2006.

Reference document 7. Jingyuan Cheng, et al, Towards Wearable Capacitive Sensing of Physiological Parameters. 2nd Int. Conf. Pervasive Computing Tech. for Healthcare, 2008.

SUMMARY OF INVENTION

The invention provides a novel method and system for generating physiological signals by using a cloth capacitive sensor, which overcomes the deficiencies of current method and system for sensing the physiology of human body. The technical problem to be solved is that the invention can be used to generate physiological signals by the cloth capacitive sensor that can sense the physiological functions of human body and can be applied to physical training, medication, fitness, entertainment etc. Specifically, at least a piece of cloth is used and provided with at least one conductive area. The conductive area is contacted with the human body. A capacitance is formed between the human body and the conductive area. A resonance frequency, voltage and current will be generated under effect of a signal provided externally. The resonance frequency, voltage and current can be used to sense the physiological parameters of the human body. In prior art, voltage changes are observed almost and the change is slight and only one position or one physiological parameter is observed. However, in the invention, physiological signals of more than one physiological parameter generated by the conductive materials in more than one position of human body or more than one physiological parameter generated by the conductive materials in only one position of human body. For example, the capacitive sensor on the neck position can detect neck rotation or swallowing by the frequency, voltage or current change. The changes are great. The wearer feels very comfortable without tight contact so that it is very practical.

Another purpose of the invention is to provide a method and system for generating physiological signals by using a novel cloth capacitive sensor. The technical problem to be solved is that the invention can sense posture of human body, the posture which can be sensed including: heat movement, leg movement or joint movement. It can be known that when the posture changes, the pressure, pull or tension changes too, so that the invention is more practical.

Another purpose of the invention is to provide a method and system for generating physiological signals by using a novel cloth capacitive sensor. The technical problem to be solved is that the invention can sense breathing, swallowing, coughing or sweating of human body so that the invention is more practical.

Further purpose of the invention is to provide a method and system for generating physiological signals by using a novel cloth capacitive sensor. The technical problem to be solved is that the invention can sense displacement, speed, acceleration, angle, angular speed, angular acceleration of human body so that the invention is more practical.

Another purpose of the invention is to provide a method and system for generating physiological signals by using a novel cloth capacitive sensor. The technical problem to be solved is that the invention can sense humidity and temperature of human body by the physiological signals generated by the cloth capacitive sensor so that the invention is more practical.

Another purpose of the invention is to provide a method and system for generating physiological signals by using a novel cloth capacitive sensor. The technical problem to be solved is that the invention can sense tension, strain, pull or pressure of human body so that the invention is more practical.

The purpose and the technical problem to be solved by the invention are realized by the following technical solution. The system for generating physiological signals by using a novel cloth capacitive sensor provided by the invention is characterized by including at least a piece of cloth, wherein at least a conductive area is arranged on the cloth. A signal circuit is provided. A capacitance is formed between the conductive cloth and the human body. When pressure, strain, pull or tension is applied between the human body and the cloth, which enables to change the capacitance or change the dielectric constant between the human body and the cloth so that the capacitance changes, the circuit sends the signal and the system receives the change in capacitance between the conductive cloth and the human body. The change is represented by frequency, voltage or current change which is used to analyze at least one piece of information of physiological and posture changes of human body, medium change between the human body and the cloth or information of force applied.

The purpose and the technical problem to be solved by the invention can be farther realized by the following technical measure.

In the system for generating physiological signals by using the cloth capacitive sensor, an elastic material is coated on the conductive cloth or the conductive cloth itself contains the elastic material.

In the system for generating physiological signals by using the cloth capacitive sensor, a switch is connected with the conductive cloth or the switch itself is the capacitive sensor.

In the system for generating physiological signals by using the cloth capacitive sensor, the switch can be a key switch, a crack switch or a multistage switch.

In the system for generating physiological signals by using the cloth capacitive sensor, different frequency, voltage or current change curves can be measured due to different physiological changes, postures or forces.

In the system for generating physiological signals by using the cloth capacitive sensor, the circuit can use a 555IC multi-oscillator, an unstable oscillating circuit by an operational amplifier, a Schmitt trigger and an unstable multi-oscillator consisting of complementary metal oxide semiconductors or transistors.

In the system for generating physiological signals by using the cloth capacitive sensor, there are at least two pieces of conductive cloth, wherein one is a reference conductive area which is grounded.

In the system for generating physiological signals by using the cloth capacitive sensor, the reference conductive area is contacted with the human body.

In the system for generating physiological signals by using the cloth capacitive sensor, the reference conductive area is formed by sewing a piece of conductive cloth on clothes, trousers, bed sheets, hats, socks, gloves or cuffs.

The system for generating physiological signals by using the cloth capacitive sensor which can be used to sense posture change can be used to measure other physiological information such as heartbeat, breathing and humidity.

In the system for generating physiological signals by using the cloth capacitive sensor, the conductive cloth is not directly contacted with the human body, and a material is set between the conductive cloth and the human body, such as a layer of cloth, rubber, plastic (TPU film), waterproof cloth, coating and printing.

The system for generating physiological signals by using the cloth capacitive sensor can be used to sense physiological changes at different positions, such as posture change, breathing, swallowing and coughing.

The system for generating physiological signals by using the cloth capacitive sensor can be used to location detection, which means that physiological or posture signals generated in a position of the human body can be known.

The system for generating physiological signals by using the cloth capacitive sensor can be used to sense at a predetermined critical pressure.

In the system for generating physiological signals by using the cloth capacitive sensor, the conductive area of the system can be further used as a physiological signal sensor, which means that electrodes can be used to sense heartbeat, breathing, brainwave, electromyography and electrocardiogram.

The system for generating physiological signals by using the cloth capacitive sensor further includes another sensor designed on the cloth.

In the system for generating physiological signals by using the cloth capacitive sensor, the conductive cloth is designed on personal clothes, such as clothes, hats, masks, socks, shoes, bed sheets, gloves, steering wheels, crutches, tablecloth, carpets or artificial limbs.

The system for generating physiological signals by using the cloth capacitive sensor can be used to sense change of dielectric constants caused by sweat, wound, sweating, medicine coating, skin powdering or cosmetics coating. As the dielectric constants change, the resonance frequencies sensed are different.

In the system for generating physiological signals by using the cloth capacitive sensor, angle, angular speed and angular acceleration of joints can be sensed by the cloth capacitive sensor.

In the system for generating physiological signals by using the cloth capacitive sensor, position, speed, acceleration or travelling distance of human can be sensed by the cloth capacitive sensor.

In the system for generating physiological signals by using the cloth capacitive sensor, pull, tension or pressure at different parts of human body can be sensed by the cloth capacitive sensor.

In the system for generating physiological signals by using the cloth capacitive sensor, displacement of human body can be sensed by the cloth capacitive sensor simultaneously.

The purpose and the technical problem to be solved by the invention are further realized by the following technical solution. The system for generating physiological signals by using a novel cloth capacitive sensor provided by the invention is characterized by including at least a piece of cloth, wherein at least a conductive area is arranged on the cloth. A signal circuit is provided. A capacitance is formed between the conductive cloth and the human body. When pressure, strain, pull or tension are applied between the human body and the cloth, which enables to change the capacitance or change the dielectric constant between the human body and the cloth so that the capacitance changes, the circuit sends the signal and the system receives the change in capacitance between the conductive cloth and the human body. The change is represented by frequency, voltage or current change which is used to analyze at least one piece of information of physiological and posture changes of human body, medium change between the human body and the cloth or information of force applied.

The purpose and the technical problem to be solved by the invention can be further realized by the following technical measure.

In the method for generating physiological signals by using the cloth capacitive sensor, an elastic material is coated on the conductive cloth or the conductive cloth itself contains the elastic material.

In the method for generating physiological signals by using the cloth capacitive sensor, a switch is further connected with the conductive cloth or the switch itself is the capacitive sensor.

In the method for generating physiological signals by using the cloth capacitive sensor, the switch can be a key switch, a crack switch or a multistage switch.

In the method for generating physiological signals by using the cloth capacitive sensor, the switch can be an analogue switch or a digital switch.

In the method for generating physiological signals by using the cloth capacitive sensor, the circuit can use a 555IC multi-oscillator, an unstable oscillating circuit by an operational amplifier, a Schmitt trigger and an unstable multioscillator consisting of complementary metal oxide semiconductors or transistors.

In the method for generating physiological signals by using the cloth capacitive sensor, there are at least two pieces of conductive cloth, wherein one is a reference conductive area which is grounded.

In the method for generating physiological signals by using the cloth capacitive sensor, the reference conductive area is contacted with the human body.

In the method for generating physiological signals by using the cloth capacitive sensor, the reference conductive area is formed by sewing a piece of conductive cloth on clothes, trousers, bed sheets, hats, socks, gloves or cuffs.

The method for generating physiological signals by using the cloth capacitive sensor which can be used to sense posture change can be used to measure other physiological information such as heartbeat, breathing and humidity.

In the method for generating physiological signals by using the cloth capacitive sensor, the conductive cloth is not directly contacted with the human body, and a material is set between the conductive cloth and the human body, such as a layer of cloth, rubber, plastic (TPU film), waterproof cloth, coating and printing. High dielectric constant, low coefficient of conductive material is preferred, such as nylon (Nylon, a relative permittivity of 3.2), silica (relative permittivity of 3.9), polyvinyl chloride (PVC, relative dielectricconstant of 3), calcium copper titanate (CCTO, the relative dielectric constant of about 10000) and other materials. The high dielectric material can be addition integrally attached to the conductor, but also may be attached on the fabric to increase. capacitive sensor effect.

The method for generating physiological signals by using the cloth capacitive sensor can be used to sense physiological changes at different positions, such as posture change, breathing, swallowing and coughing.

The method for generating physiological signals by using the cloth capacitive sensor can be used to location detection, which means that physiological signals generated in a position of the human body can be known.

The method for generating physiological signals by using the cloth capacitive sensor can be used to sense at a predetermined critical pressure.

In the method for generating physiological signals by using the cloth capacitive sensor, the conductive area of the system can be further used as a physiological signal sensor, which means electrodes.

The method for generating physiological signals by using the cloth capacitive sensor further includes another sensor designed on the cloth.

In the method for generating physiological signals by using the cloth capacitive sensor, the conductive cloth is designed on personal clothes, such as clothes, hats, masks, socks, shoes, bed sheets, gloves, steering wheels, crutches, tablecloth, carpets or artificial limbs.

The method for generating physiological signals by using the cloth capacitive sensor can be used to sense change of dielectric constants caused by sweat, wound, sweating, medicine coating, powdering and make-up. As the dielectric constants change, the resonance frequencies sensed are different.

In the method for generating physiological signals by using the cloth capacitive sensor, angle, angular speed and angular acceleration of joints can be sensed by the cloth capacitive sensor.

In the method for generating physiological signals by using the cloth capacitive sensor, position, speed, acceleration or travelling distance of human can be sensed by the cloth capacitive sensor.

In the method for generating physiological signals by using the cloth capacitive sensor, pull, tension or pressure at different parts of human body can be sensed by the cloth capacitive sensor.

In the method for generating physiological signals by using the cloth capacitive sensor, physiological information of human body can be sensed physiology by the cloth capacitive sensor.

In the method for generating physiological signals by using the cloth capacitive sensor, gait stability of human body can be sensed by signal change generated by sensors on feet.

In the method for generating physiological signals by using the cloth capacitive sensor, gait of human body can be analyzed by the cloth capacitive sensor.

In the method for generating physiological signals by using the cloth capacitive sensor, actigraph of human body can be sensed by the cloth capacitive sensor.

In the method for generating physiological signals by using the cloth capacitive sensor, fall of human body can be judged by the cloth capacitive sensor.

In the method for generating physiological signals by using the cloth capacitive sensor, gait stability is measured by change of center of mass, center of mass speed or center of mass acceleration.

In the method for generating physiological signals by using the cloth capacitive sensor, different frequency, voltage or current change curves can be measured through different physiological statuses measured by the cloth capacitive sensor.

In the method for generating physiological signals by using the cloth capacitive sensor, displacement at different parts of human body can be sensed by the cloth capacitive sensor.

In the method for generating physiological signals by using the cloth capacitive sensor, structure of the conductive cloth is like a Velcro structure.

In the method for generating physiological signals by using the cloth capacitive sensor, a resistor R, a capacitor C or an inductor L is connected in series or in parallel with the cloth capacitive sensor to change the signal range of frequency, voltage or current.

In the method for generating physiological signals by using the cloth capacitive sensor, switches are connected in series or in parallel with the cloth capacitive sensor.

Compared with the prior art, the invention has remarkable advantages and benefits. By means of above technical solution, the method and system for generating physiological signals by using the cloth capacitive sensor provided by the invention at least have the advantages and benefits as follows:

In the prior art, change of voltage is almost observed, the change is slight and only a single parameter or a single position is read. However, in the invention, change of frequency, voltage or current is observed under effect of pressure, tension, pull or strain. And the frequency, voltage or current change of different physiological parameters in a same position or different positions is great, when the invention is used, the wearer will feel very comfortable without tight contact.

In conclusion, the invention relates to method and system for generating physiological signals by using the cloth capacitive sensor. In the system, a capacitance is formed between the electrodes of cloth and human body which are contacted. Under an effect of a signal provided externally, when pressure, tension, pull or strain is applied between the human body and the cloth, which enables to change the capacitance or change the dielectric constant between the human body and the cloth so that the capacitance changes, change of the capacitance is sensed. The change of capacitance is displayed by frequency, voltage or current so that a frequency, voltage or current change will be generated. Change of resonance frequency, voltage or current is used to respond physiological parameters of human body, such as posture, swallowing, coughing, breathing, sweating, even heartbeat etc. The invention makes remarkable progress in technology and has obvious active effect, which is a novel, advanced and practical design.

The description is just the summary of the technical solution of the invention. In order to under the technical means of the invention more clearly so as to implement according content of the description and in order to obviously and easily understand the above and other purposes, characteristics and advantages of the invention, better embodiments are exemplified particularly and matched with drawings, details as follows.

BEST EMBODIMENTS OF INVENTION

Figure 1:
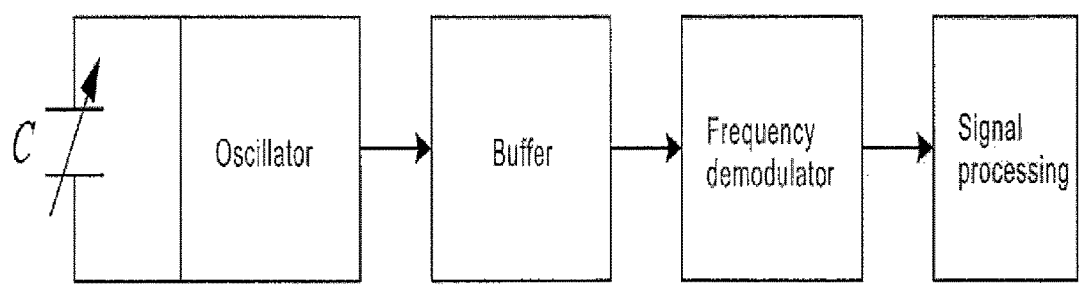
FIG. 1 is a framework schematic diagram of the invention.

In order to further illustrate the technical means and functions adopted by the invention to achieve predetermined purposes, in the following drawings and best embodiments, the method and system for generating physiological signals by using the cloth capacitive sensor provided by the invention, and embodiments, structure, method, steps, characteristics and functions thereof are described in details as follows.

The preceding and other technical contents, characteristics and functions of the invention can be clearly represented in the following detailed specification of better embodiments matched with reference drawings. Through description of embodiments, it is understandable to obtain a deeper and specific realization of technical means and functions adopted by the invention to achieve predetermined purposes. However, the drawings are only for reference and description and not used to limit the invention.

Technology of the invention has been contributed to title "Capacitive textile sensor detecting physiological signal by resonance frequency" of IEEE EMBC 2010. Meanwhile, this technology can be used to make various sensors on clothes be connected in series or in parallel with the capacitive sensor of the invention by human body monitoring system of texture sensor so that information obtained is not only physiological signals, but also analogue signals at different parts of human body under external forces, pressure, tension, center of mass or pull, such as humidity, pressure, breath etc. Therefore, gait analysis or signals of physiological parameters such as heartbeat, breathing, physiology, body temperature etc. are more accurate.

The measurement theory of the invention lies in forming an ideal capacitance which consists of two conductive plates separated and insulated from each other by an electric medium. The capacitance (C) is defined as charge (Q)/voltage (V). The capacitance is dependent on area of conductive plates, distance therebetween and material of electric medium.

Human body can be regarded as a conductor. When conductive cloth is contacted with surface of human body, that is, a capacitance is generated between skin and cloth electrodes. Therefore, when the body status changes, center of mass, pressure, tension or strain between the body and the conductive cloth change, too. Thus, the capacitance between the body and the conductive cloth changes as well, that is to say, physiological changes will lead to sensible change of capacitance. In the invention, the conductive cloth is contacted with skin and when pressure is applied to the conductive cloth, the capacitance will change too. We have designed an oscillator to generate signals. When there are physiological changes, that is pressure, center of mass, torsion or pull are applied between the body and the cloth which change, the capacitance will change as well. Therefore, we can sense changes of resonance frequency, voltage or current. It can be used to sense changes on physiological parameters or postures.

We have designed an oscillator to generate signals. Once there is physiological or pressure changes, the capacitance will be changed too. Thus, we can sense changes of resonance frequency, voltage or current so as to differentiate the capacitance between skin and cloth electrodes or external forces applied. The whole system' structure is represented as follows, wherein variable capacitance C is change in capacitance of human body. In addition, frequency demodulator can be replaced by circuit that measures voltage or current of the capacitance for the maximum sensible range of frequency change is $2\pi f$, such as resonance frequency of 50 HKz, the frequency locking range reaching about 12.5 KHz maximally. When the frequency change range is large, sectional frequency locking is adopted or frequency is directly counted. Meanwhile, result can be analyzed through signal processing.

Figure 2:
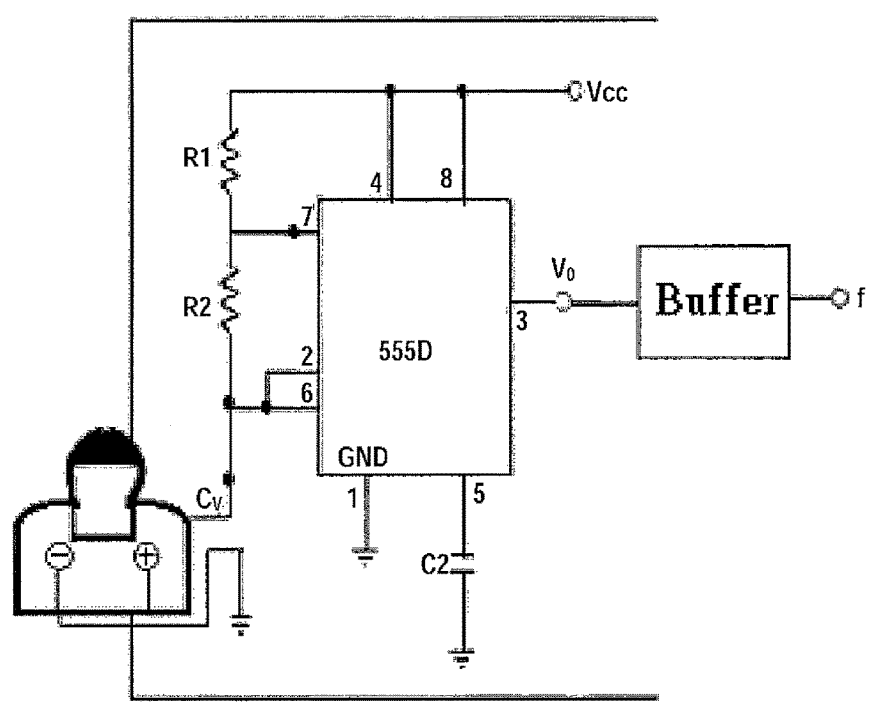
FIG. 2 is a schematic diagram of measurement theory and resonance frequency of the invention.
Figure 3:
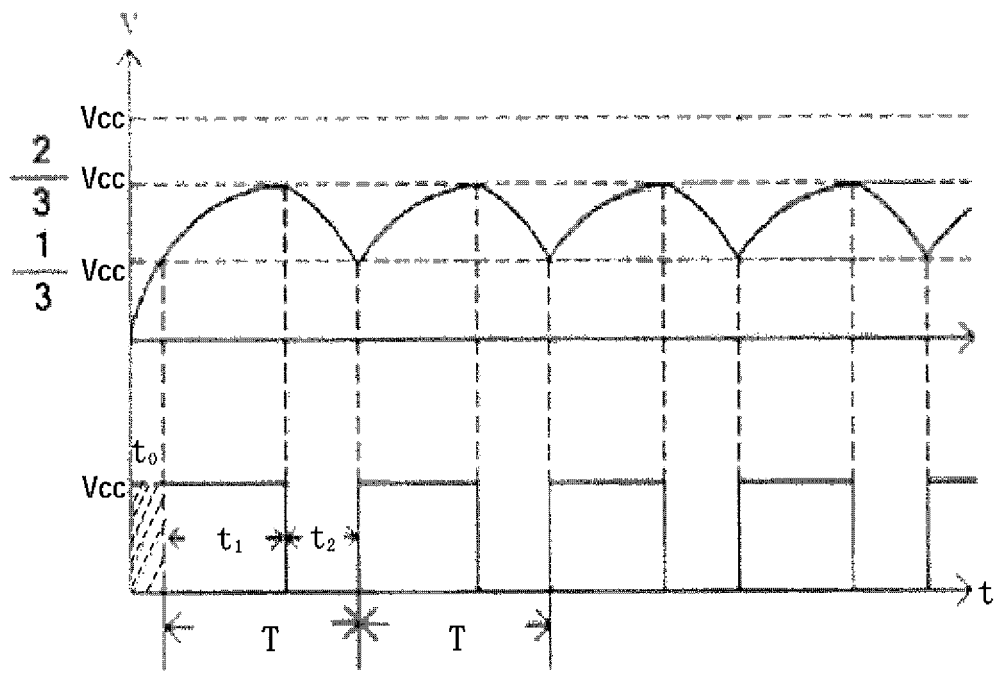
FIG. 3 is a schematic diagram of charge-discharge process and corresponding output of the invention.

System structure of the invention is represented in FIG. 2. 555IC is used to form a stable multi-oscillator circuit. External circuit comprises R1, R2, Cv and bypass capacitor C2 that eliminates noise. When power supply is initially connected, the capacitor Cv is not charged and the third pin output of 555 is high voltage. Capacitor Cv is charged through R1 and R2. When it is charged to $\frac{2}{3}$ Vcc, the sixth pin of 555 is triggered to act so that the third pin output is converted to low potential (0V). At the same, capacitor Cv must be discharged through R2 (the third pin output is "Low", which is regarded as grounded). When Cv is discharged to $\frac{1}{3}$ Vcc, the second pin is triggered so that the third pin output is further converted to high potential again. Thus, oscillation in cycles is performed. C2 is the bypass capacitor, which is unnecessary for control. It serves to prevent external noise from inputting from the pin to 555 to cause 555's fault. Charge and discharge process of Cv and corresponding output are represented in FIG. 3.

A capacitor C1 is formed by human skin and cloth electrodes. Variation of capacitor will change the capacitance. Therefore, we replace Cv of stable multi-oscillator circuit by means of the characteristic. This is because the physical change on contact pressure between cloth electrodes and skin has the equivalent effect of changeful capacitor Cv.

Capacitance between skin and cloth sensor under external force will change, which means capacitor C1 is changeful under pressure. Changeful capacitor is balanced through a stable multi-oscillator circuit. But there are different frequencies that we desire. Meanwhile, common current flowing through body is about 165 µA (R1 and R2 are 10 Kohm, Vcc is 3.3V).

Oscillating Frequency $$f = \frac{1}{T} = \frac{1.4}{(R_1 + 2R_2)C_1} \quad (1.1)$$

Figure 4:
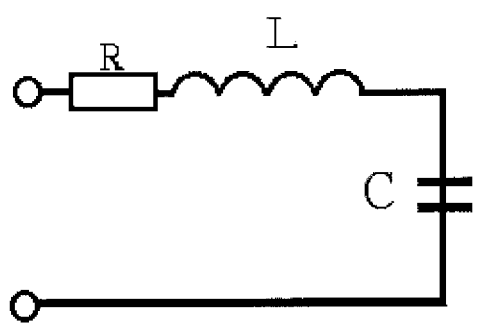
FIG. 4 is a schematic diagram of equivalent circuit of capacitive sensor of the invention.

Equivalent circuit of capacitive sensor is shown as FIG. 4. The capacitor C is the change in capacitance of physiological parameters or postures etc. measured under different conditions of human body, wherein at least a piece of cloth is provided with at least a conductive area contacted with human body under the external forces, pressure, pull, tension or center of mass. R is resistor in the circuit and L is inductor in the circuit. Different R and L can be sewed on the cloth to obtain different signal values.

Figure 5:
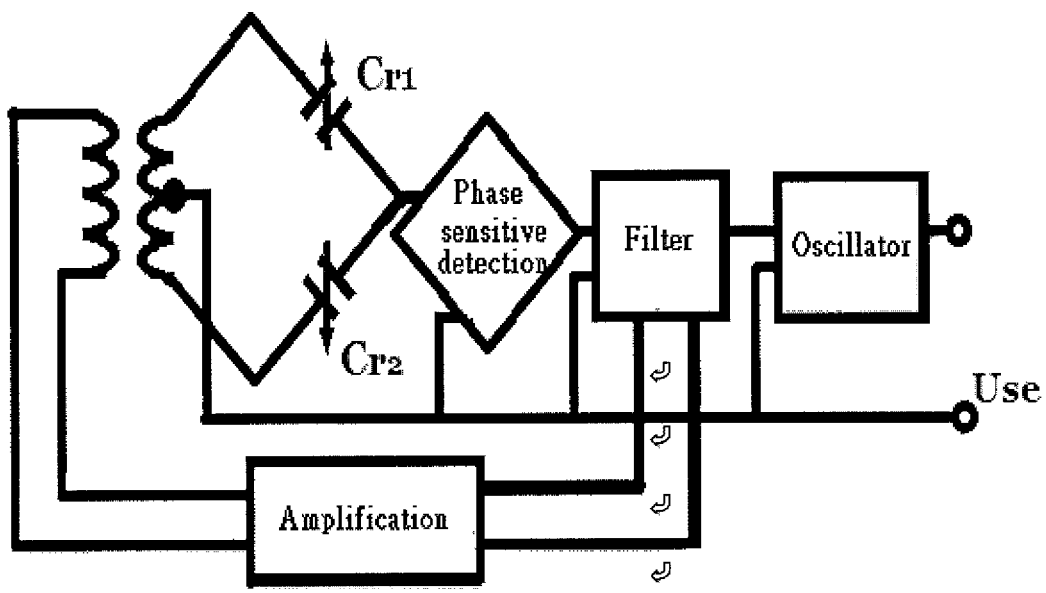
FIG. 5 is a schematic diagram of electric bridge measurement circuit of the invention.

The following is an example that shows measurable circuit. Besides 555IC, electric bridge circuit can be used as shown in FIG. 5. Cr1 and Cr2 are two capacitors which can be arranged in two positions of the body, such as tiptoe and heel of the foot. Gait change of the tiptoe and heel during walk can be represented by changes of output voltage ($U_{SC}$), current or frequency. Obviously, we also can regard Cr1 as a fixed capacitor and use Cr2 to measure physiological signals of human body under external forces, pressure, pull or tension.

Figure 6:
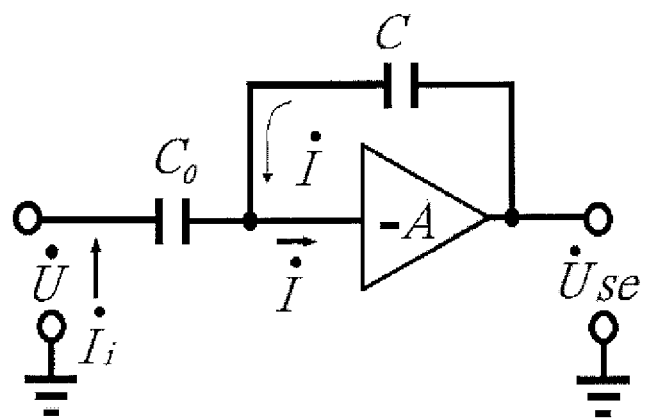
FIG. 6 is a schematic diagram of measurement circuit of operational amplifier of the invention.

Measurement circuit of another capacitive sensor is a circuit of operational amplifier shown as FIG. 6, wherein U is input voltage, Usc is output voltage, I is input current, Ix is feedback current, Cx is sensor and C0 is fixed capacitor.

When input impedance of the operational amplifier is high and gain is great, the input current of the operational amplifier can be regarded as zero. According to Kirchhoff law:

$$\dot{U}_0 = -\dot{U}_i \frac{C_0}{C_x}$$

Thus, when pressure, tension or strain are different, capacitance Cx changes therewith, which means output voltages are different. Obviously, we can regard Cx and C0 as capacitances of the human body in different positions or Cx is fixed capacitor and C0 is a capacitor used to sense signal of human body.

If the sensor is regarded as a parallel plate capacitor, $$C_x = \frac{\varepsilon S}{d},$$

wherein S is area of conductive cloth, $\varepsilon$ is dielectric constant between the conductive cloth and human body and d is distance between the human body and the cloth plate.

It is clear that the output voltage of the operational amplifier is in positive proportion to the distance d between the electrodes and the human body. Of course, we can regard C0 as another capacitor between the conductive cloth and the human body and view change of the two points (Cx and C0)) along with time, C0 is not a fix value.

Figure 7:
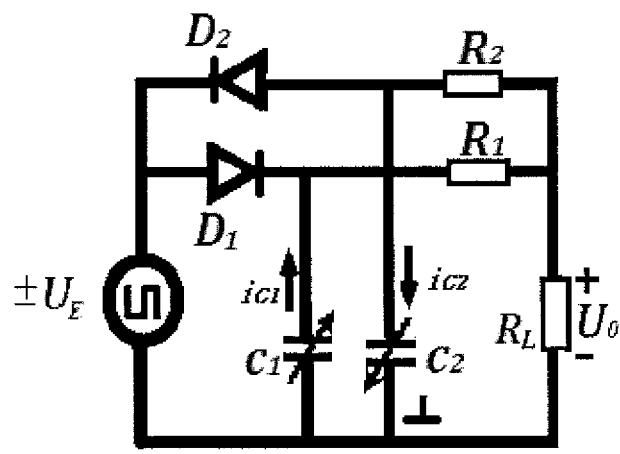
FIG. 7 is a schematic diagram of double T-shaped circuit of diode of the invention.

Another circuit is a double T-shaped circuit of diode shown as FIG. 7, wherein UE is input voltage, D1 and D2 are diodes, and RL is load resistor. In positive semi-cycle, diode D1 is conducted, D2 is cut off, and capacitor C1 is charged to UE in an extremely short time. Voltage initial value of capacitor C2 is UE. Power supply supplies power to RL by iC1 through R1 while capacitor C2 is discharged through R2 and RL. Discharge current flowing through RL is iC2 and total current flowing through RL is iL which is algebraic sum of iC1 and iC2.

Average current on capacitor C1:

$$I_{C1} = \frac{1}{T} \frac{R + 2R_L}{R + R_L} U_E C_1$$

Voltage generated on load $R_L$:

$$U_0 = \frac{RR_L}{R + R_L}(I_1 - I_2) = \frac{RR_L(R + 2R_L)}{(R + R_L)^2} \frac{U_E}{T}(C_1 - C_2)$$

When $R_L$ is given, $$\frac{RR_L(R + 2R_L)}{(R + R_L)^2}$$

is constant and ordered as K, $$U_0 \approx K \cdot f \cdot U_E \cdot (C_1 - C_2)$$

Output voltage is not only related to frequency and amplitude of power supply voltage, but also to difference of capacitors C1 and C2. When the power supply voltage is determined, the output voltage is just a function of capacitors C1 and C2. So, we can fix a capacitor to measure the capacitor change of another capacitor change on the body or measure changes of the two capacitor changes from the body. In addition, differential pulse width modulation circuit can be used to obtain same result.

Figure 8:
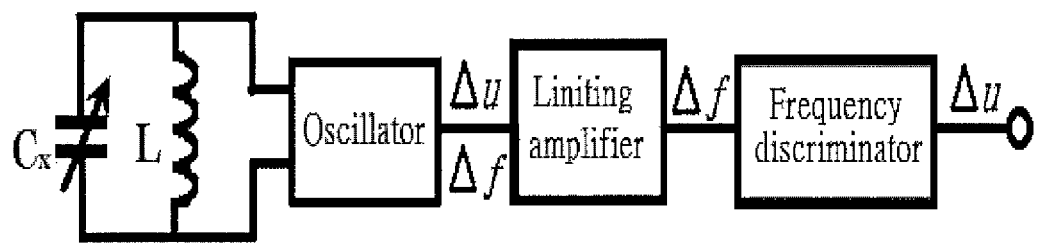
FIG. 8 is a functional block diagram of FM measurement circuit of the invention.

We can further use FM circuit shown as FIG. 8, $$f = \frac{1}{2\pi\sqrt{LC}}$$

and $C=C_1+C_0+C_c$ (C1: fixed capacitor of oscillating loop, C0: sensor capacitor, Cc: lead distribution capacitor), so that change of frequency f can be measured according to change of C0.

Figure 9:
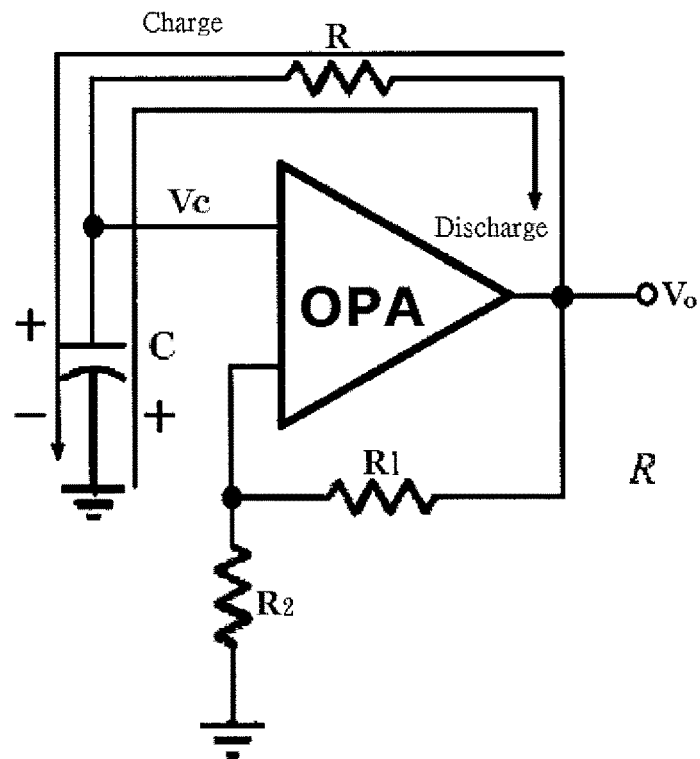
FIG. 9 is a schematic diagram of oscillating circuit of OPA which is unstable of the invention.
Figure 10:
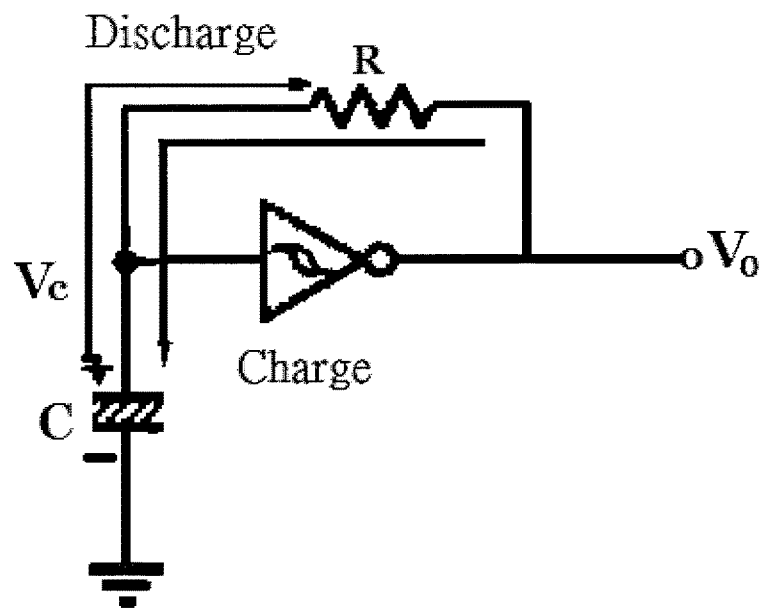
FIG. 10 is a schematic diagram of unstable multi-oscillator consisting of Schmidt trigger of the invention.
Figure 11:
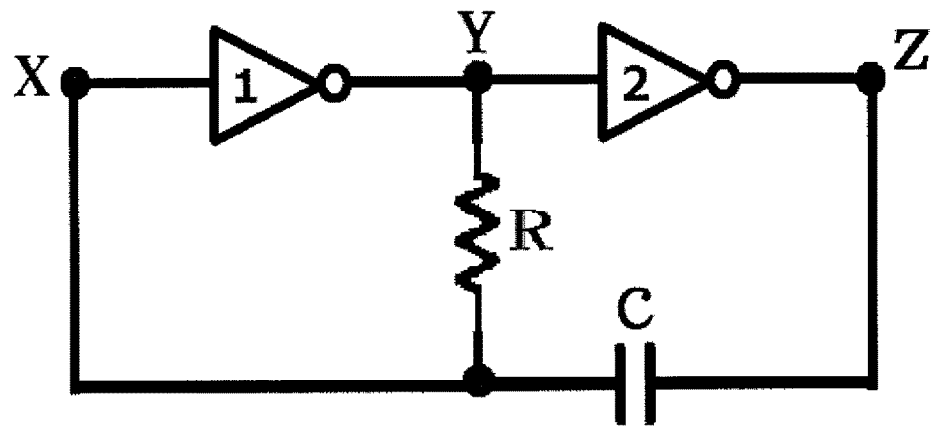
FIG. 11 is a schematic diagram of unstable multi-oscillator consisting of CMOS of the invention.
Figure 12:
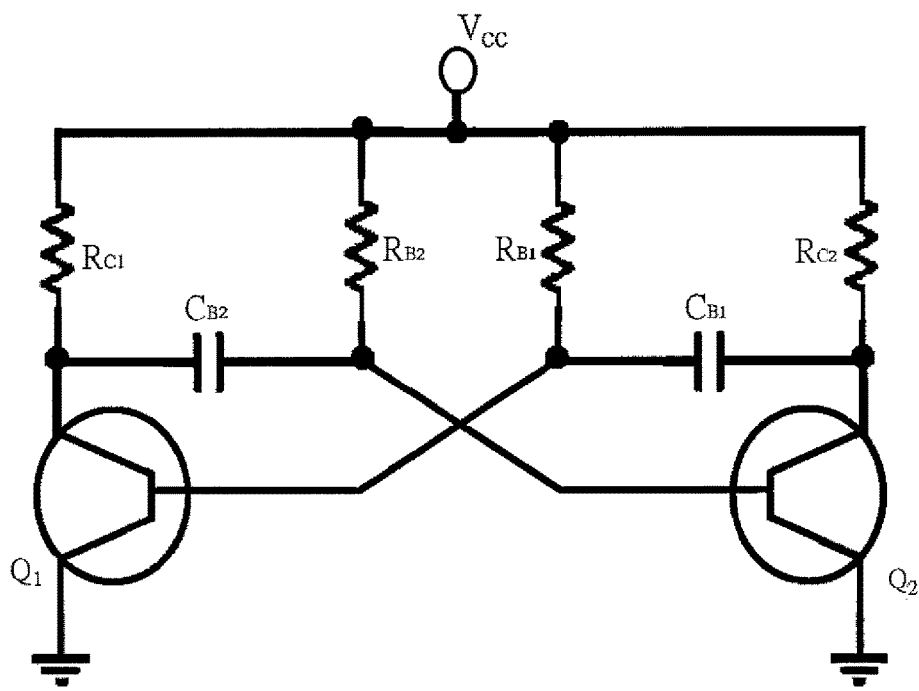
FIG. 12 is a schematic diagram of unstable multi-oscillator consisting of transistors of the invention.

Unstable multi-oscillator can oscillate without adding triggering signals and belongs to an auto-excitation type multi-oscillator. The above is multi-oscillator with 555IC. We can further use OPA as unstable oscillating circuit (shown as FIG. 9). Its frequency F-1/2RC ln(1+2R$_2$/R$_1$). In the body at different positions such as amplifiers on chest and abdomen, its R1, R2 and R values are different so that same change in capacitance will generate different frequency response results, that is to say, different resistors on the cloth can generate different output voltage, current or frequency values. Therefore, we can measure different resonance frequencies on the cloth by different R1 and R2 values, that is to say, in different positions of body such as tiptoe and heel matched with different R1 and R2 values, the values of resonance frequencies are different. Even if changes of capacitance C at that time are same, the changes can be used for gait analysis. Same principle can be applied to monitoring other physiological signals. In addition, unstable multi-oscillator (shown as FIG. 12) can further consist of Schmidt trigger (shown as FIG. 10) or CMOS (shown as FIG. 11) or transistors. In FIG. 12, there are two capacitors C1 and C2, which respectively represent capacitive sensors at tiptoe and heel. So, capacitance change of tiptoe and heel during gait analysis can be represented by frequency change.

Material of conductive area of the cloth capacitive sensor used can be conductive materials, such as conductive yarns (stainless steel yarns, silver yarns etc.), conductive wires (stainless steel wires, copper wires etc.), conductive plate sheets (stainless steel sheets, nickel, chromium metal sheets and etc.) or other conductive materials, such as conductive silicon materials, graphite, conductive polymolecular materials which are arranged on the cloth by different ways, such as:
1. weaving non-conductive fiber and conductive fiber together by way of a textile process, wherein the textile process is knitting, weaving, tatting, embroidering or other proper processes;
2. formed by embedding, bonding or sewing conductive sheets into the cloth;
3. formed by sewing the conductive filament into the cloth;
4. formed by coating or adhering conductive substances on the cloth;

5. formed by bonding or sewing conductive textile on the cloth.

The above non-conductive fiber can be but not limited by cotton, fiber, nylon etc. The conductive fiber can be but not limited by polymolecular conductive fiber or conductive metal fiber, and blended by stainless steel fiber and non-conductive fiber or formed by coating or permeating conductive substances on insulating fiber. The conductive materials account for 1-100% of the conductive area.

The following embodiments are illustrated by 555IC (shown as FIG. 2) as an example.

Embodiment I

Shift of frequency can be read by means of contact of single silver fiber and hand skin shown as tables 1-1 and 1-2.

TABLE 1-1 single conductive area test

| | Silver fiber sponge | | Stainless steel conductive cloth | |
|---|---|---|---|---|
| | No touch | 1 Kg | 5 Kg | 10 Kg |
| Testee A | 110 | 70 | 75 | 70 | KHz |
| Testee B | 110 | 75 | 75 | 70 | |

TABLE 1-2 single conductive area test

| | Silver fiber cloth electrodes | | | |
|---|---|---|---|---|
| | Slight touch | 20 Kg | 30 Kg | |
| Testee A | 85.65 | 84 | 81.15 | KHz |
| Testee B | 70.03 | 70.57 | 73.45 | |

Figure 13:
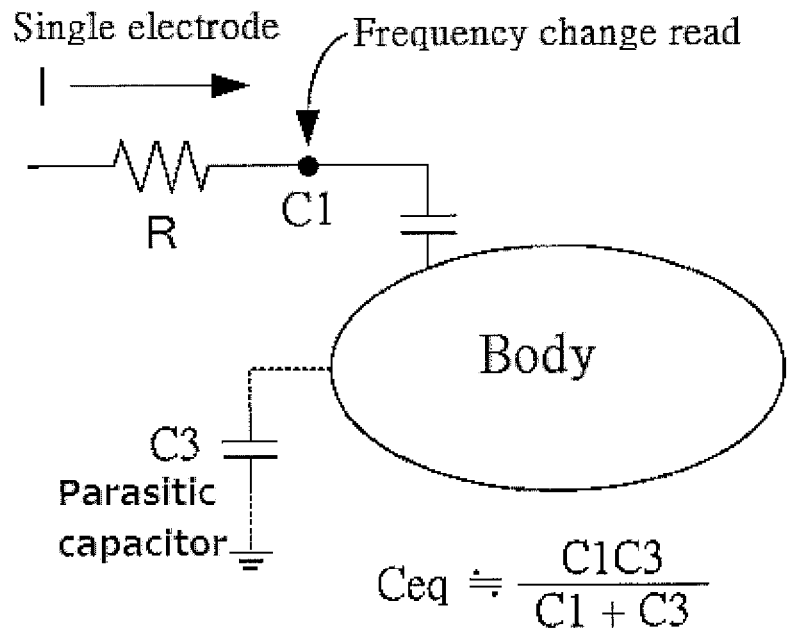
FIG. 13 is a schematic diagram of single electrode silver fiber cloth electrode implementation of the invention.

As the result of table 1-1 and table 1-2, we can explain the model shown as FIG. 13. Under normal circumstances, impedance of body skin is about 500-1000 ohm, so that human body is regarded as good conductor. Therefore, change of frequency only represents change in capacitance between the conductive cloth and skin. But, the body itself has an equivalent parasitic capacitor C3, and the capacitance (C3) value is smaller than the capacitance of capacitor C1 between the skin and the cloth in the conductive area. As Ceq of equivalent capacitor measured is connected in series with C1 and C3, and its value is Ceq≈C1C3/C1+C3. In the period, C3 is small. Total value is about C1. Therefore, frequency change is not obvious under pressure change. Shown as table 1-1, if silver fiber cloth is coated with sponge, when there are no external forces, that is to say the silver fiber cloth is not contacted with skin, the frequency is 110 KHz. Under pressure of 1 kg, frequency between the skin and silver fiber coated with sponge is 70 KHz. If the silver fiber coated with sponge is replaced by stainless steel conductive cloth, the frequency under external force of 5 kg is 75 KHz, and that under 10 kg is 70 KHz. The stainless steel conductive cloth is structured so that the cotton cloth is contacted with skin while the other cloth not contacted with skin is sewed with stainless steel fiber, which means there is no direct contact between skin and conductive area but the skin and conductive area is isolated by cloth.

Shown as table 1-2, the frequency measured on testee A who slightly touches with force of 20 KG, 85 KHz is 84 KHz while the frequency measured under force of 30 Kg, 85 KHz is 81 KHz. Therefore, change of frequency is not obvious under change of external force. Meanwhile, different results are obtained due to different people. For some people, value obtained increases along with pressure while for others, signal value decreases along with increasing pressure.

Embodiment II

Two conductive areas are used to be contacted with skins of two hands. One hand is contacted with the cloth of the conductive area while the other hand is contacted with the conventional electrodes as the cloth of the conductive area. The conventional electrodes are connected with ground of circuit.

Figure 14:
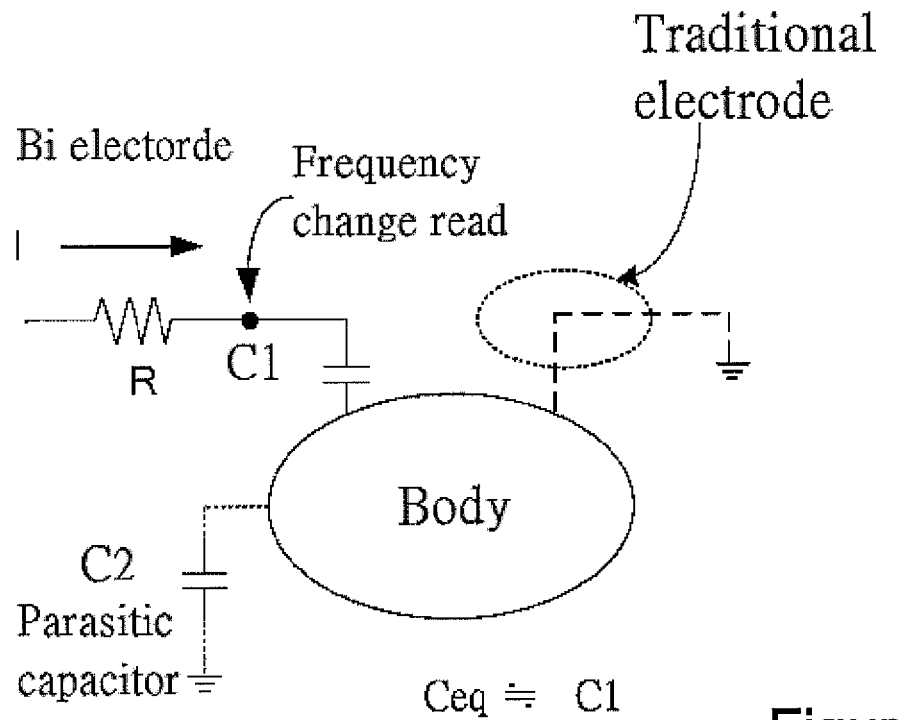
FIG. 14 is a schematic diagram of two cloth electrodes contacted with skin wherein one is a conventional electrode of the invention.

Data is shown as tables 2-1 and 2-2. Table 2-1 is the result obtained by using single silver fiber cloth. Table 2-2 is the result obtained by using silver fiber cloth coated with sponge as electrodes. The data model is shown as FIG. 14. For one hand is contacted with the conventional electrodes, the capacitance between the conventional electrodes and human body is nearly 0. The capacitance between the conventional electrodes and human body will lead to relative short circuit of parasitic capacitor C3 so that the equivalent capacitance Ceq of the whole system is approximately equal to C1.

Data in actual operation is shown as follows. In table 2-1, when the silver fiber cloth is slightly contacted with electrodes, the frequency is 1.534 KHz. When pressure of 20 Kg is applied to the silver fiber cloth, the frequency is 978 Hz. When pressure of 30 Kg is applied to the silver fiber cloth, the frequency is 976 Hz.

In table 2-2, the silver fiber cloth coated with sponge is used as electrode. When the electrode is slightly touched, the frequency is 1.24 KHz. When 20 kg is applied to the electrode, the frequency is 0.69 KHz. When 30 kg is applied to the electrode, the frequency is 0.68 KHz. It can be known from the result that the conductive cloth coated with sponge has better effect and frequency response generated by the conductive cloth coated with sponge under external force is very remarkable. Conductive cloth material under moist state to connect with ground circuit can obtain the same result.

TABLE 2-1

| | Silver fiber cloth | | | |
|---|---|---|---|---|
| | Slight touch | 20 Kg | 30 Kg | |
| Testee A | 1.53 | 0.98 | 0.98 | KHz |
| Testee B | 1.45 | 0.85 | 0.83 | |

TABLE 2-2

| | Silver fiber cloth | | | |
|---|---|---|---|---|
| | Slight touch | 20 Kg | 30 Kg | |
| Testee A | 1.24 | 0.69 | 0.68 | KHz |
| Testee B | 1.15 | 0.42 | 0.38 | |

TABLE 2-3

| | Short fiber stainless steel cloth | | | | | | | |
|---|---|---|---|---|---|---|---|---|
| | Slight touch | 5 Kg | 10 Kg | 20 Kg | 30 Kg | 40 Kg | 50 Kg | |
| Testee A | 110 | 83 | 73 | 60 | 53 | 48 | 45 | KHz |
| Testee B | 110 | 44 | 34 | 26 | 21 | 18 | 17 | |

Figure 15:
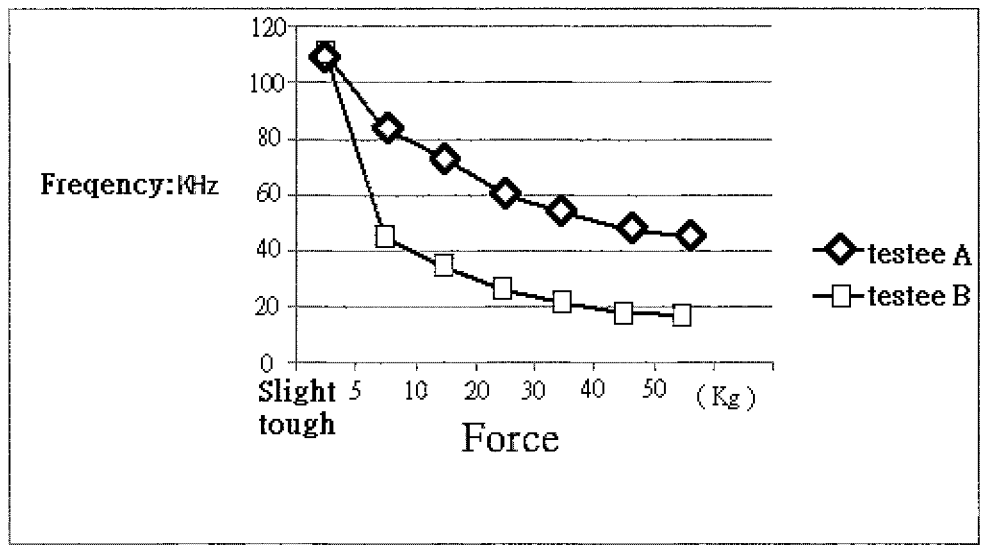
FIG. 15 is a schematic diagram of frequency change of the invention when weights changes, two electrodes, one is the short fiber stainless steel cloth electrode and the other conventional electrode is grounded.

Shown as table 2-3, if silver fiber cloth is replaced by short fiber stainless steel cloth, the frequency under 5 kg is 83 KHz, 73 KHz under 10 kg, 60 KHz under 20 kg, 53 KHz under 30 kg, 48 KHz under 40 kg, and 45 KHz under 50 kg. It can be seen that the capacitance of silver fiber cloth is greater than that between stainless steel short fiber cloth and human body so that the frequency reaction curve shown as FIG. 15 does not change immediately under increasing external force. The short fiber stainless steel cloth consists of non-conductive cloth sewed with conductive fiber such that the part contacted with human body is cotton cloth sewed with short fiber stainless steel fiber (5% of stainless steel fiber) while cotton not contacted with human body is sewed with long fiber stainless steel fiber.

Embodiment III

Two conductive areas are used to be contacted with skins of two hands. One piece of cloth of the conductive area is made by silver fibers while the other is silver fiber cloth coated with sponge. The result is similar to those of table 2-1 and table 2-2. But better effect is obtained by placing sponge electrodes. Frequency variation between the two conditions is remarkable.

Figure 16:
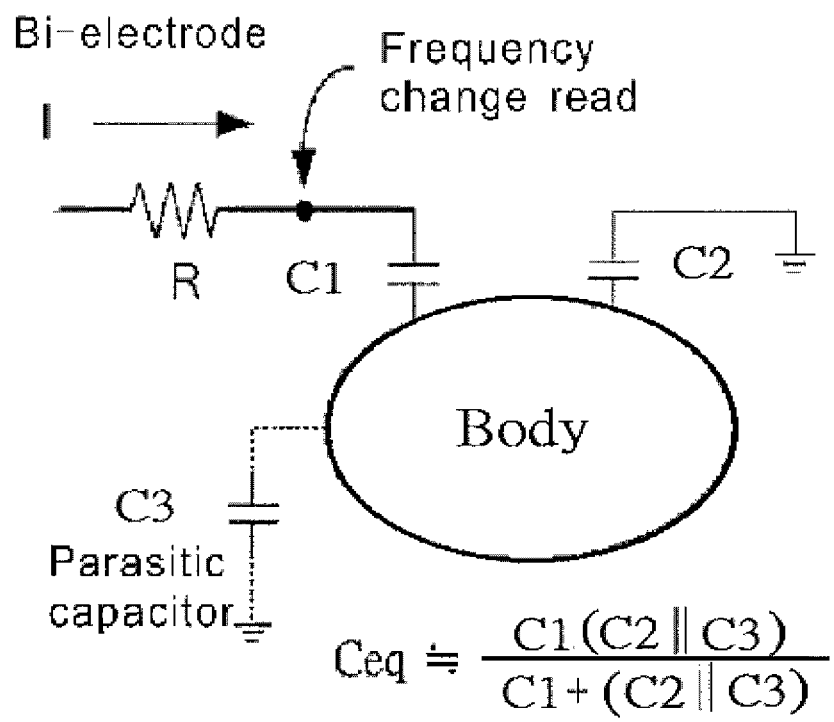
FIG. 16 is a schematic diagram of two cloth electrodes contacted with skin of the invention.

Our data is shown as tables 3-1, 3-2 and 3-3. In table 3-1, two pieces of silver fiber cloth are used, in table 3-2, one piece of sliver fiber cloth is used while silver fiber cloth coated with sponge is used, and in table 3-3, two pieces of silver fiber cloth coated with sponge are used. The data model is shown as FIG. 16. Because two pieces of cloth in the conductive area used as electrodes are contacted with skin to generate C1 and C2, there are C1, C2 and parasitic capacitor C3 of the human body in the whole system. Therefore, the equivalent capacitance Ceq is approximately equal to:

$$Ceq \approx \frac{C1(C2 \parallel C3)}{C1 + (C2 \parallel C3)}.$$

Data in actual operation is shown as follows. In table 3-1, two pieces of silver fiber cloth are used and when the electrodes are slightly touched, the frequency is 11 KHz. When pressure of 20 Kg is applied to the electrodes, the frequency is 5.6 KHz. When pressure of 30 Kg is applied to the electrodes, the frequency is 5.2 KHz.

Figure 17A:
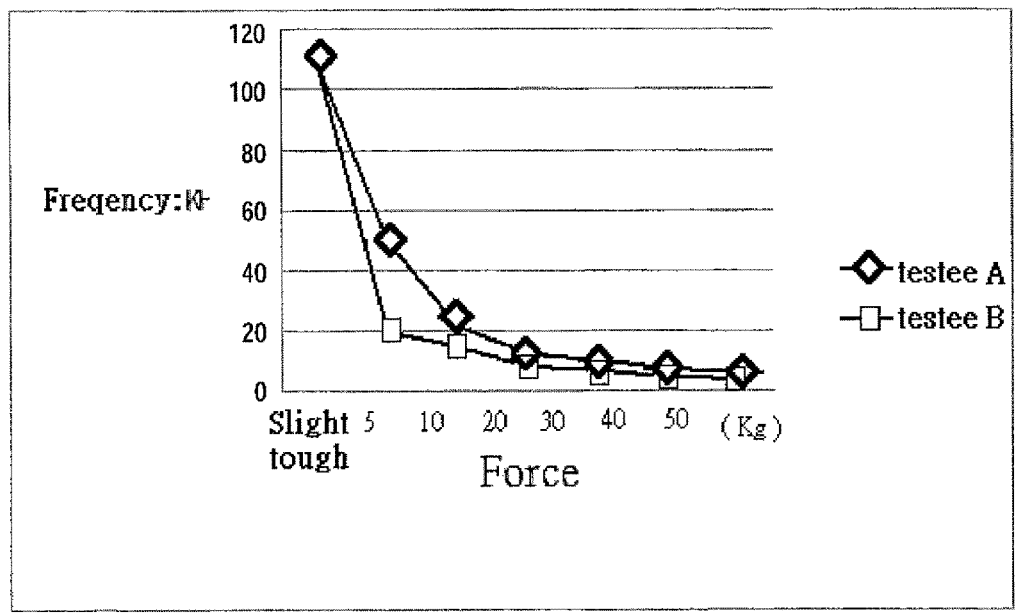
FIG. 17A to 17B are schematic diagrams of changes of weight and frequency of short fiber stainless steel cloth and silver fiber when the other silver fiber cloth is grounded.
Figure 17B:
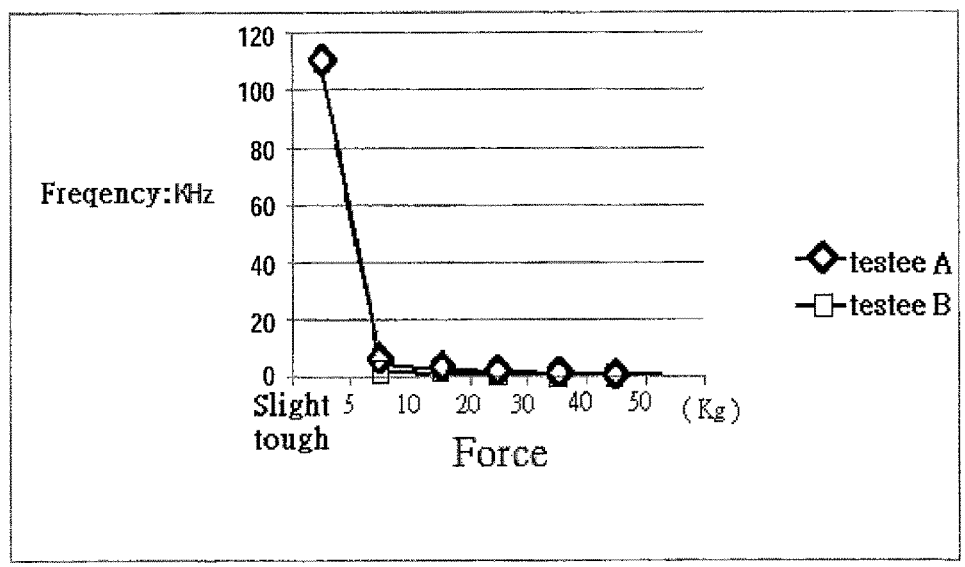

In table 3-3, the silver fiber cloth coated with sponge is used as electrodes. When the electrodes are slightly touched, the frequency is 110 KHz; when pressure of 20 Kg is applied to the electrodes, the frequency is 3.6 KHz; when pressure of 30 Kg is applied to the electrodes, the frequency is 3.3 KHz. Pressures are applied to signal end but grounded end. It can be seen from the result that conductive cloth coated with sponge has better effect than that without sponge. The elastic material can be sponge, rubber, elastic piece, spring, silicon material etc, which means conductive materials are different in elasticity or different in capacitances under same pressure, pull or strain when coated with different elastic materials, thus leading to different frequency, voltage or current responses. Shown as tables 3-4 and 3-5, when the electrode, that is to say, the grounded end is stainless steel fiber cloth which is sewed at the opening of socks, and short fiber stainless steel cloth is sewed at heel of socks under no pressure, the frequency under pressure of 5 kg for testee A is 50 KHz, that under pressure of 10 kg for testee A is 22 KHz, that under pressure of 20 kg for testee A is 12 KHz, that under pressure of 30 kg for testee A is 10 KHz, that under pressure of 40 kg for testee A is 7.5 KHz and that under pressure of 50 kg for testee A is 6 KHz. If silver fiber is sewed at the heel, the frequency under pressure of 5 kg is 5 KHz, that under pressure of 10 kg A is 3 KHz, that under pressure of 20 kg A is 2.1 KHz, and that under pressure of 30 kg A is 1.7 KHz. Frequency variations are shown as FIGS. 17A and 17B. It can be seen from the curve that capacitance between silver fiber cloth and human body under external forces is sensitive and does not respond soon, so that elastic materials such as sponge is necessary to sense change of external forces, pressure, pull or tension.

In addition, if the grounded electrode is good conductor such as silver fiber or 100% conductive fiber, signal change of output capacitance is not obviously when good conductor electrode is at the grounded end and the electrode is force applied. And it has obvious change when cloth in conductive area at the end connected with the signal line used as electrode is applied, shown as table 3-6. In particular, when good conductor is not used at signal line end, the signal change is more obvious, for example, short fiber stainless steel conductive cloth or low proportional conductive material averagely distributed on the cloth, like 5% good conductor and stainless steel fiber which are sewed on common non-conductive cloth. In addition, the grounded electrode can do not connect with ground of to the circuit.

TABLE 3-1

| | Silver fiber cloth | | | |
| --- | --- | --- | --- | --- |
| | Slight touch | 20 Kg | 30 Kg | |
| Testee A | 11 | 5.6 | 5.2 | KHz |
| Testee B | 11 | 5.6 | 4.3 | |

TABLE 3-2

| | Silver fiber cloth | | | |
| --- | --- | --- | --- | --- |
| | Slight touch | 20 Kg | 30 Kg | |
| Testee A | 11 | 7.2 | 5.5 | KHz |
| Testee B | 11 | 5.4 | 4.3 | |

TABLE 3-3

| | Silver fiber cloth | | | |
| --- | --- | --- | --- | --- |
| | Slight touch | 20 Kg | 30 Kg | |
| Testee A | 11 | 3.6 | 3.3 | KHz |
| Testee B | 11 | 3.2 | 3.1 | |

TABLE 3-4

| | Short fiber stainless steel cloth | | | | | | |
| --- | --- | --- | --- | --- | --- | --- | --- |
| | Slight touch | 5 Kg | 10 Kg | 20 Kg | 30 Kg | 40 Kg | 50 Kg |
| Testee A | 110 | 50 | 22 | 12 | 10 | 7.5 | 6 | KHz
| Testee B | 110 | 20 | 15 | 8 | 7 | 5 | 4 |

TABLE 3-5

| | Silver fiber cloth | | | | | | |
|---|---|---|---|---|---|---|---|
| | Slight touch | 5 Kg | 10 Kg | 20 Kg | 30 Kg | 40 Kg | 50 Kg | |
| Testee A | 110 | 5 | 3 | 2.1 | 1.7 | 1.7 | 1.7 | KHz |
| Testee B | 110 | 1.76 | 1.4 | 1.2 | 1.16 | 1.16 | 1.16 | |

TABLE 3-6

| | Not pressed | Press grounded end only | Press signal end only | Press both ends | |
|---|---|---|---|---|---|
| Silver fiber | 110 | 110 | 6 | 1.5 | KHz |
| Short fiber stainless steel conductive cloth | 110 | 110 | 9 | 8 | |

Embodiment IV

Figure 18:
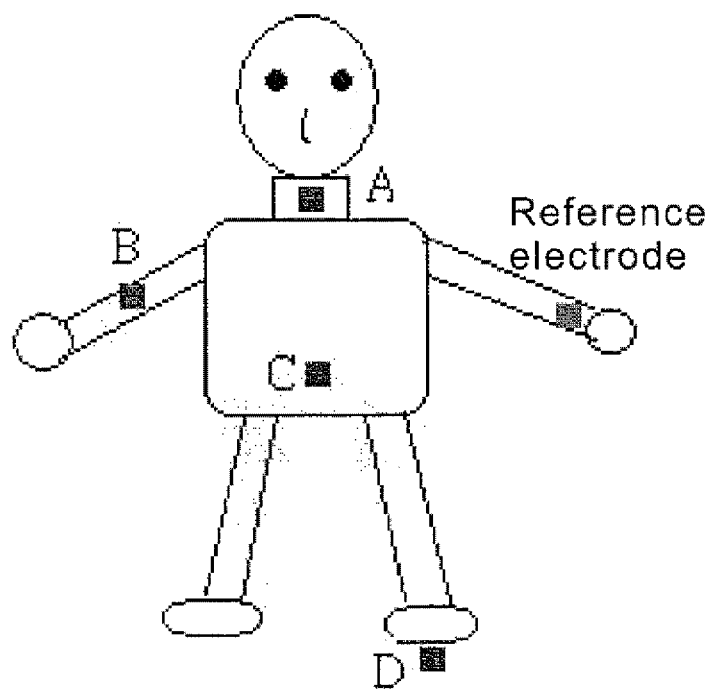
FIG. 18 is a schematic diagram of physiological changes measured by body.

We use silver fiber conductive cloth without sponge in the conductive area and sew it around the cuff at wrist as a reference point (ground of circuit). Many pieces of silver fiber cloth coated with sponge are used as conductive areas placed in other parts of the body to sense signals of physiological changes. The main physiological phenomenon measured includes breath, the measuring position marked as C in abdomen; swallowing and coughing measuring position is marked as A in neck, posture change measuring position is marked as A in neck, B in elbow and D in feet shown as FIG. 18.

A represents the conductive cloth sewed at throat area, B the conductive cloth placed at elbow area, C the conductive cloth placed in abdomen area and D the conductive cloth placed in socks or shoes.

Electrode A is sewed at throat area for measure frequency changes caused by swallowing and coughing.

Figure 19:
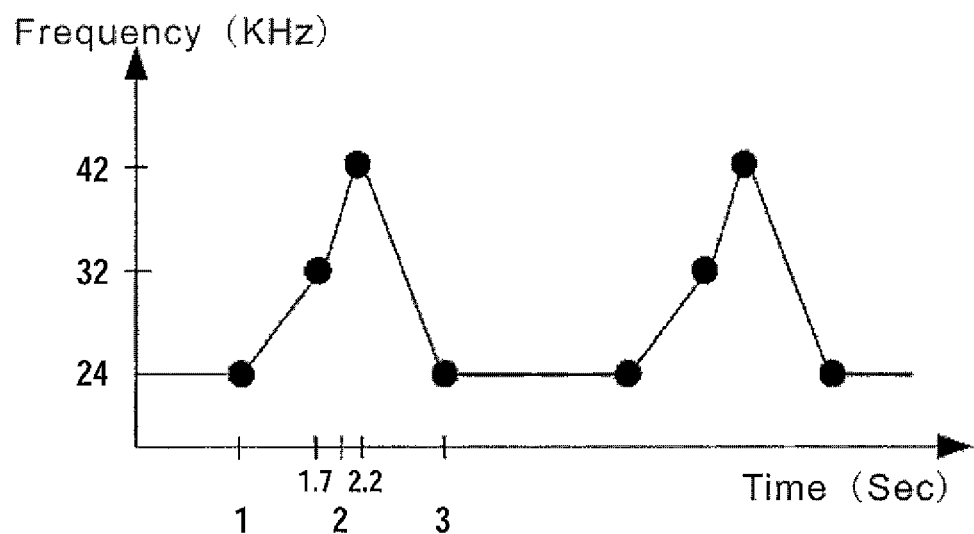
FIG. 19 is a schematic diagram of changes of swallowing frequency and time of the invention.
Figure 20:
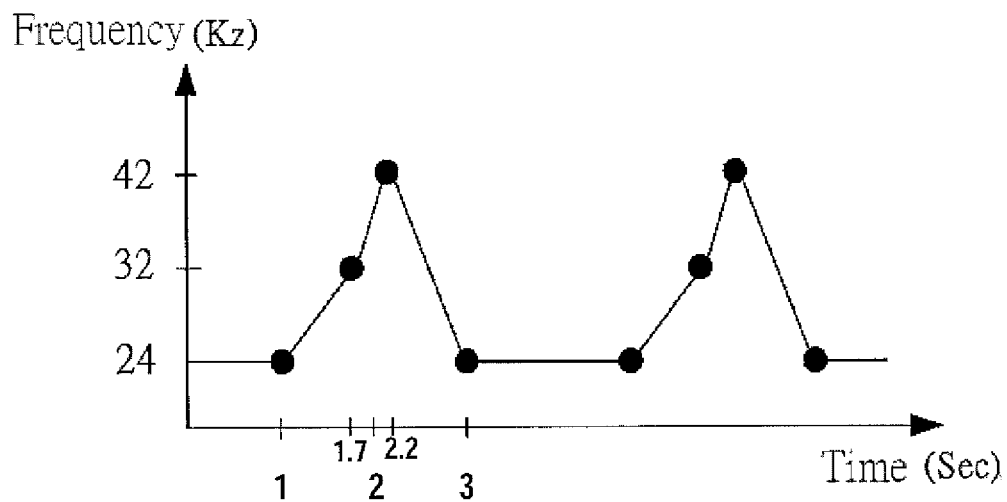
FIG. 20 is a schematic diagram of changes of coughing frequency and time of the invention.

During swallowing, frequency smoothly increased when spittle enters throat from oral cavity from 24 to 32 KHz. However, when spittle enters into the throat, the frequency is pulled up to 42 KHz immediately and dramatically. The maximum value occurs just when spittle enters into throat. After swallowing, the frequency returns to 24 KHz again. The whole process costs about 2 seconds shown as FIG. 19. The swallowing processes of people share a same characteristic, which means that the basic frequency is no change when swallowing is not performed, frequency is pulled up slowly to some frequency level, then a large frequency change occurs as soon as possible and finally the frequency returns to the original basic frequency again. During coughing, the basic frequency of the testee is originally 75 KHz when he is not coughing, and the frequency will change immediately to 82 KHz when he is coughing. After coughing, the frequency returns to about 75 KHz. The whole process costs about 1 second. Time for the frequency change is transient and change is remarkable. But during the whole process, the frequency moves up and down the basic frequency shown as FIG. 20.

It can be seen from two sequence charts that during swallowing, the frequency will increase slowly; then the frequency will be pulled up immediately and return to original frequency after swallowing. The time on change is the time spent to swallow. But coughing is instantaneous frequency change and the change is around original frequency. The time on change is short, which is the time spent on coughing. Therefore, we can differentiate swallowing from coughing by means of different sequences.

An electrode is placed behind neck. When the testee straights the neck, the basic resonance frequency is 56 KHz; when the testee fades way at 30 degrees, the basic resonance frequency becomes 51 KHz; when the testee fades way at 60 degrees, the basic resonance frequency becomes 49 KHz. Then the testee straights the neck again and the basic resonance frequency returns to 56 KHz. The conductive area is placed in front of the neck. When the testee lowers his head at 25 degrees downward, the resonance frequency becomes 52 KHz; when he straights the neck, the resonance frequency returns to 56 KHz. The variable process is smooth. We can judge the movement of neck by the frequency change. For example, angular speed can be calculated by whether the neck bends forward or backward, the bending angle and time spent. Furthermore, angular acceleration among head bends at different times can be calculated similarly. The conductive area is placed at the neck and distinguishes swallowing, coughing and speaking as well as movement of the neck.

The cloth B in the conductive area is arranged at elbow to measure movement of the elbow. The other conductive area is sewed around the clothes and not coated by elastic material and used as reference conductive area which is to be grounded. The frequency changes measured are as follows:

When the elbow is unbent, the frequency measured is about 120 KHz. When the elbow bends inward to 30 degrees, the frequency starts to change and the frequency measured at the time is 102 KHz. When the elbow bends to 90 degrees, the frequency is 75 KHz shown as table 4-1. Movement of the elbow can be acquired by the signal. In this process, the frequency change is in positive correlation to the bending angle of the elbow so that we can estimate the bending angle of the elbow by means of the characteristic, so as to further obtain the angular speed and angular acceleration. Similarly, the frequency can be measured for other joints that bend or elongate. For example glove, the other conductive cloth is sewed at index finger in the glove, and the result is shown as table 4-2. It can be seen that the frequency is 110 KHz when the index finger does not bend, that is 44 KHz when the index finger bends to 150 degrees, that is 37 KHz when the index finger bends to 120 degrees, that is 23 KHz when the index finger bends to 90 degrees and that is 9 KHz when the index finger bends completely. Therefore, the bending change or the finger and its parameters such as angle, angular speed and angular acceleration can be measured by means of different frequency responses caused by different tensions (pulls) when movements of the finger in the glove are different. The grounded conductive cloth can be sewed at the opening of the glove and the same result can be obtained.

TABLE 4-1

| | Angle | | | | | |
|---|---|---|---|---|---|---|
| | 0° | 30° | 45° | 90° | 135° | |
| Frequency | 120 | 102 | 90 | 75 | 67 | KHz |

TABLE 4-2

| | Angle | | | | |
|---|---|---|---|---|---|
| | 0° | 30° | 60° | 90° | Bend completely |
| Frequency | 110 | 44 | 37 | 23 | 9 | KHz |

The cloth C in the conductive area is arranged at abdomen to measure breathing and the frequency changes are as follows: the reference conductive area is sewed on clothes in underarm position.

Figure 21:
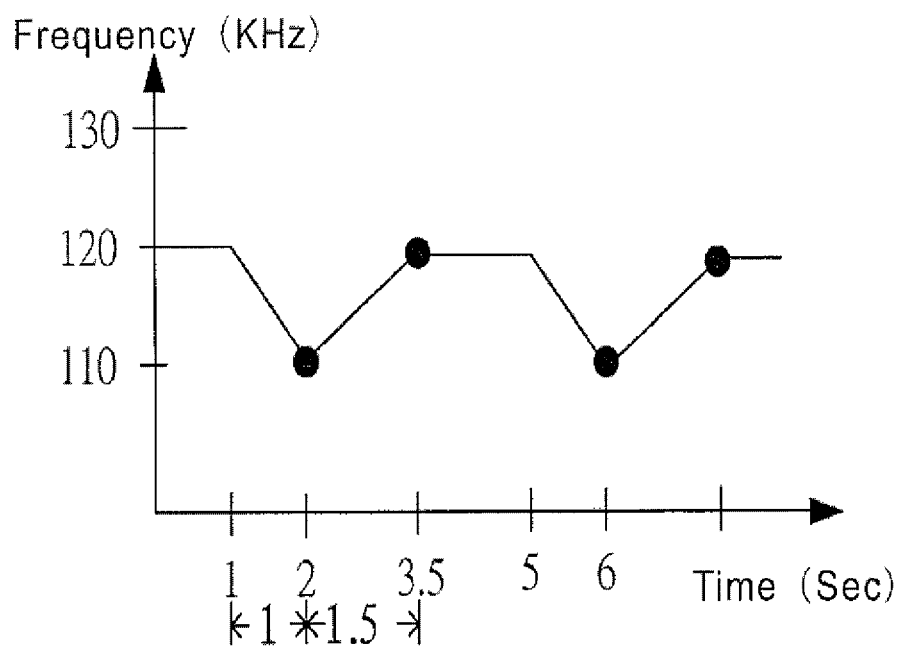
FIG. 21 is a schematic diagram of changes of breathing frequency and time of the invention.

When there is no any movement, the frequency measured is 120 KHz. When "inhale" at the top, that is to say inhale completely, the frequency measured is about 110 KHz and inhalation spends 1 second; when "inhale" to the end, the frequency measured is about 120 KHz and inhalation spends 1.5 seconds. The process is substantially regular and repeated. During deeper breathing, the maximum frequency shifts down, for example, the frequency in this case is lower than 110 KHz. Then the frequency returns to original basic frequency which is about 120 KHz. Therefore, inhaling time, exhaling time, breathing frequency and breathing depth can be measured shown as FIG. 21.

The cloth D in the conductive area is arranged at feed to measure treading. The reference conductive area is arranged near the topmost part of the socks. The frequency changes are described as follows:

When the testee slightly touches the conductive area at the heel, the resonance frequency is 120 KHz, when the testee starts to step on the electrode, the frequency begins to decrease (the minimum frequency is 32 KHz), and force applied to the feet is 7 Kg. Following increasing weight change will cause no great frequency change. In the process that feet leave the conductive area slowly, the resonance frequency returns to 120 KHz from 32 KHz. It is high in repeatability. That is to say, when the testee walks, the instantaneous basic frequency by stepping down will decrease rapidly and the frequency will return to the basic frequency when the testee uplifts the feet. Therefore, we can know how many steps the testee makes. If the conductive cloth is sewed at the heel of the socks and foot is suspended, when the foot bends downward, the frequency is 110 KHz. When the foot is placed flatwise, the frequency is 97 KHz. And the frequency is 22 KHz when the foot is uplifted. Frequency change can be equivalently generated by means of tension change of socks affected by upward or downward movement of the foot. Therefore, the frequency can be used to measure the movement change of the foot. At the same time, the other conductive cloth is sewed at the tiptoe of the socks. When the foot bends downward, the frequency is 110 KHz and the tension of socks is minimum. When the foot is placed flatwise, the frequency is 87 KHz and when the foot is uplifted, the frequency is 18 KHz and the tension of socks is maximum show as table 4-3. It can be seen from above that whether the heel or tiptoe of the socks is sewed with the conductive area, the frequency will change because the tension of the socks changes by means of movement at the sole of the foot. The frequency value can be used to reversely deduct the movement of foot. Meanwhile, if the cloth in the conductive area is sewed at heel and tiptoe, we thus know the stepping speed and the acceleration of right and left feet that change due to known length of socks and signals of front and back cloth capacitive capacitors on the socks during walk. And the distance during the walking time can be known for the distance S is equal to ($V*t+\frac{1}{2}$ acceleration$*t^2$) or displacement change "S" is measured under coordinates of speed and time. Therefore, the capacitive sensors are arranged on the socks or shoes to measure signals of gait analysis. If the capacitive sensors are arranged at knee or the positions of the body such as hand, hip, and elbow, the measurement can be more accurate. Pressure at the sole of the foot or change on center of mass of the testee during walk can be known.

TABLE 4-3

| | Movement | | |
|---|---|---|---|
| | Bend downward | Place flatwise | Uplift |
| Heel | 100 | 97 | 22 | KHz |
| Tiptoe | 112 | 87 | 18 | |

Analysis of center of mass is analysis of stability of walking gait, which is the analysis by sequence charts generated by sensors at feet. Change on center of mass, center of mass speed and center of mass acceleration of people walking can be observed by change on analysis signals generated by sensors at feet so as to obtain the gait stability of user.

Figure 22:
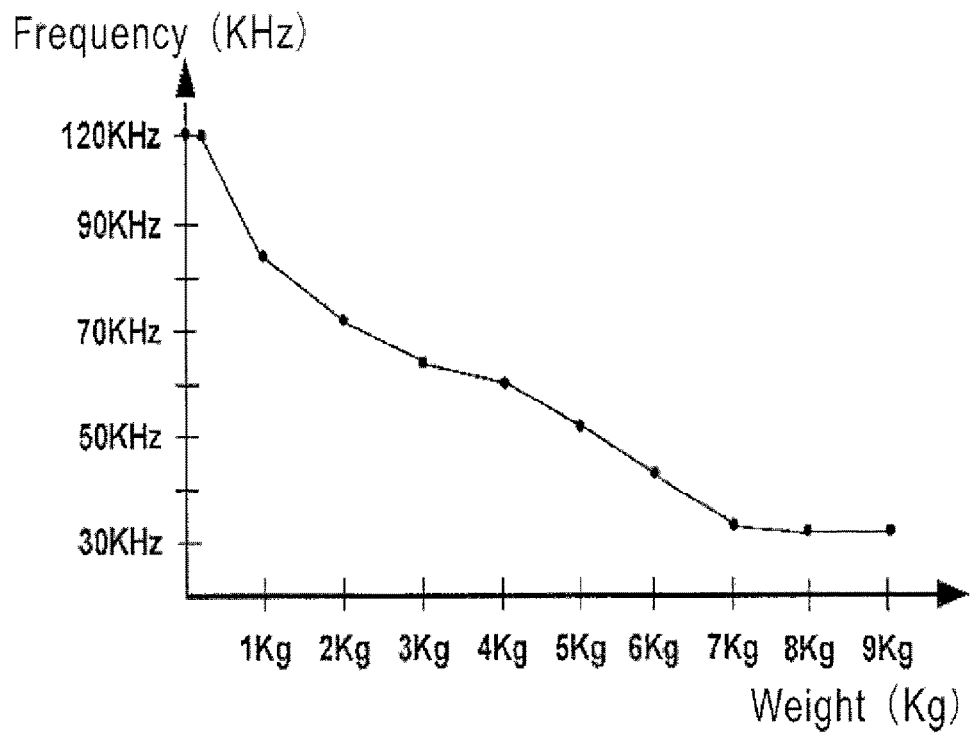
FIG. 22 is a schematic diagram of frequency change when foot weight changes of the invention.

Shown as FIG. 22, as stepping time changes rapidly, we can judge whether the testee walks or runs by means of period of frequency change caused by treading. Therefore, we can analyze gait of the testee and judge whether the testee falls or not by the sensor, which means that the cloth capacitive sensor can be used to sense falling.

As more than one capacitive sensor is arranged on the clothes, for example, at front, back, left and right sides of the clothes, when the user sleeps, signals change due to different sleeping positions such as front sleeping position, left side sleeping position and sleeping position with face down which press different sensors. The sensor at chest is on when the testee sleeps in front sleeping position and holds arms, but the signal change is different from that of the sensor obtained by just sleeping in front position or sleeping with face down. Therefore, the signal change of the capacitive sensor can be used to sensor the posture and its change of sleep and generate the actigraph at the same time.

Physiological signals can be generated by the cloth capacitive sensor and variability of the physiological signals of the user can be obtained.

The capacitive sensor can be used to sense posture and other physiological signals such as heartbeat, breathing, body temperature and humidity etc.

Embodiment V

In the following, we use at least three conductive areas (a reference conductive which is grounded and at least two signal conductive areas of measuring signals). For example, one signal conductive area is arranged at the elbow while the other one is arranged at the heel, which are respectively used to measure signals at the two points. The frequency changes measured will be smaller and can be measured. Substantially, the capacitance of conductive area of originally one measuring signal is C, its variation in the measuring process is delta C. If another conductive area of one measuring signal is available, its capacitance is C+C1. C1 is capacitance increased by another conductive area of one measuring signal. The total variation in the measuring process is still about $\Delta C$ and relative variation is $\Delta C/(C+C)$ which is smaller than the variation $\Delta C/C$ of conductive area of originally one measuring signal. It still can be read. Thus, we can use an oscillator to send frequency to sense the physiological changes at different positions of the body at the same time. For example, we use at least three conductive areas (a reference conductive which is grounded and at least two signal conductive areas for measuring signals) to measure signals of posture change, breathing, swallowing, coughing, heartbeat, humidity or body temperature, etc.

For example, three measuring conductive areas are connected at the signal end, which are respectively silver fiber (pressed by index finger), short fiber stainless steel cloth (pressed by middle finger) and pure stainless steel conductive cloth (weaved completely by stainless steel fiber and pressed by ring finger). When the three conductive areas are taken as three different cloth capacitive sensors to measure the capacitance, the grounded end is connected with the silver cloth (a reference conductive area is grounded). When different measuring capacitance combinations are applied by fingers of 3 KG respectively, the results are shown as table 5-1. When pressed independently, the frequency of silver fiber is minimum for the conductive coefficient of silver fiber is maximum and relative capacitance is maximum. The conductive coefficient of short fiber stainless steel cloth capacitive sensor is minimum among the three. Compared with the other two, the capacitance is relatively far smaller. Therefore, when the short fiber stainless steel cloth capacitive sensor is connected in series, no greater impact on total capacitance is posed and relative variation is on the other two. When the three are pressed, because the area contacted with the body is maximum, the capacitance is maximum and the frequency is minimum. Thus, if the cloth capacitive sensors of different characteristics are used to measure the capacitance, physiological changes or posture changes at different positions can be sensed at the same time, which means there is more than one signal conductive area of the cloth capacitive sensors.

TABLE 5-1

| Material | Frequency |
| --- | --- |
| Silver fiber | 1.3 |
| Short fiber stainless steel cloth | 10.4 |
| Pure stainless steel conductive cloth | 1.6 |
| Silver fiber + short fiber stainless steel cloth | 0.95 |
| Short fiber stainless steel cloth + pure stainless steel conductive cloth | 1.1 |
| Silver fiber + pure stainless steel conductive cloth | 0.75 |
| Press the three | 0.5 |
| | KHz |

Embodiment VI

Short fiber stainless steel cloth is pressed by a fixed force of 5 KG, water of 0.02 cc is orderly dipped by a syringe and different humidity and frequency changes are shown as table 5-2. It can be seen that when water reaches 0.06 cc, the frequency starts to decrease. Therefore, relative humidity can be obtained according to frequency change, which means the invention can be used as a humidity sensor. The cloth capacitive sensor can be used humidity sensor under different pressures, pulls or strain.

TABLE 5-2

| Humidity | | | | | | | | | | |
| --- | --- | --- | --- | --- | --- | --- | --- | --- | --- | --- |
| 0 | 0.02 | 0.04 | 0.06 | 0.08 | 0.1 | 0.12 | 0.14 | 0.16 | 0.18 | 0.2 cc |
| Frequency 115 | 115 | 115 | 90 | 57 | 30 | 17 | 12 | 9 | 6.2 | 5.2 KHz |

Embodiment VII

When the conductive cloth such as silver fiber is sewed at thumb and index finger of the glove, and the hand does not move (the hand opens), the frequency measured is 14 KHz. When the thumb bends at 90 degrees, the frequency measured is 9 KHz, when the index finger bends at 90 degrees, the frequency measured is 6 KHz, and when the thumb and index finger bend at 90 degrees, the frequency measured is 4 KHz. Therefore, movement of fingers can be measured by capacitance change generated by the capacitive sensors of the glove stressed shown as table 5-3. Certainly, we sew the conductive cloth at other finger joints to measure movement of the hand. Based on same principle, we can express sign language by table 5-3 and sense signal characteristics and behavior process of the hand holding articles such as chopsticks, spoon, cigarette, umbrella, supporting handle, and pen etc.

TABLE 5-3

| | All do not move | Thumb moves | Index finger moves | All move | |
| --- | --- | --- | --- | --- | --- |
| Frequency | 14 | 9 | 6 | 4 | KHz |

Embodiment VIII

The conductive cloth is sewed at the heel and tiptoe of socks. The grounded conductive cloth is sewed at the opening of the socks. When the testee walks, the frequency is 62 KHz when foot is suspended. The frequency is 111(Hz when the heel just touches the ground. The frequency is 6.7 KHz when center of mass proceeds completely on the foot. The frequency is 3.8 KHz when the tiptoe just touches the ground. The frequency is 2.1 KHz when the center of mass falls completely on the foot. The frequency is 2.8 KHz when the heel is to leave the ground. The frequency is 3.3 KHz when the tiptoe touches the ground. The instantaneous frequency is 5.2 KHz when center of mass is shifted to the other foot and the tiptoe leaves the ground first. The frequency is 62 KHz again when the foot is suspended shown as table 5-4. Signal changes of left and right feet can be used to obtain walking distance, speed and acceleration and further pressure change and center of mass change at the sole during walk. Therefore, gait analysis can be measured by the method with capacitance sensing. If the conductive cloth is further sewed on trousers at knee, gait can be analyzed by more signals measured. Certainly, the capacitive sensors arranged at more positions can obtain more information. Combined with embodiment VI, the capacitive sensor can sense pressure and humidity to analyze gait or posture change.

TABLE 5-4

| | Suspended | Heel just touches the ground | Center of mass shifts forward | Tiptoe just touches the ground | Step on completely | At the moment the heel leaves the ground | Only the tiptoe touches the ground | At the moment the tiptoe leaves the ground | |
|---|---|---|---|---|---|---|---|---|---|
| Frequency | 62.5 | 11 | 6.7 | 3.8 | 2.1 | 2.8 | 3.3 | 5.2 | KHz |

Embodiment VIIII

When the conductive cloth is sewed at both sides of the underarm parts of jacket, the inner conductive cloth is contacted with the body and the outer conductive cloth is contacted with skin of arm, and the two pieces of conductive cloth will press each other when the hand hangs down. The inner or outer conductive cloth can be further provided with sponge to increase the thickness. The conductive cloth is sewed at the collar to be grounded. When the hand hangs down, the frequency is 0.2 KHz. When the hand is lifted up at 15 degrees, the frequency is 0.25 KHz, when the hand is lifted up at 30 degrees, the frequency is 0.3 KHz, when the hand is lifted up at 45 degrees, the frequency is 0.4 KHz, when the hand is lifted up at 60 degrees, the frequency is 0.45 KHz, when the hand is lifted up at 75 degrees, the frequency is 3 KHz and when the hand is lifted up at 90 degrees, the frequency is 24 KHz. Therefore, the capacitive sensors can be used to sense swinging state of arm such as angle, angular speed and angular acceleration shown as table 5-5. Similarly, the method can be further used to measure movement of left and right legs. At the time, two pieces of conductive cloth are sewed at crotches of trousers at both sides.

TABLE 5-5

| | Angle | | | | | | | |
|---|---|---|---|---|---|---|---|---|
| | 0° | 15° | 30° | 45° | 60° | 75° | 90° | |
| Frequency | 0.2 | 0.25 | 0.3 | 0.4 | 0.45 | 3 | 24 | KHz |

Therefore, we can sense the physiological signals or posture changes at different positions by way of measuring several sensors with a signal source, such as limb movement signals which can be analyzed. Certainly, we can provide independent oscillators at different measuring positions or signals at different positions by a same oscillator at different times to sense. That is to say, only one sensor at a same time senses the physiological signals. By above shown method, signal change range of frequency, voltage or current can be changed by changing resistor R, capacitor C or inductor L on the line so that the physiological signals or posture changes at different positions can be analyzed. We not only know the physiological signals or posture changes but also understand where the signal is generated from the body.

Embodiment X

We have arranged a switch on the conductive area to select appropriate part to retrieve the physiological signals according to postures of the human body so as to separate noise caused by incorrect touch effectively and close the power supply of the primary sensor, thereby saving electricity and energy. The switch can be further used to position, which means that physiological signals generated in a position of the human body can be known. The switch further can accurately measure values of frequency, voltage or current corresponding to change of pressure, tension, pull or strain.

Figure 23A:
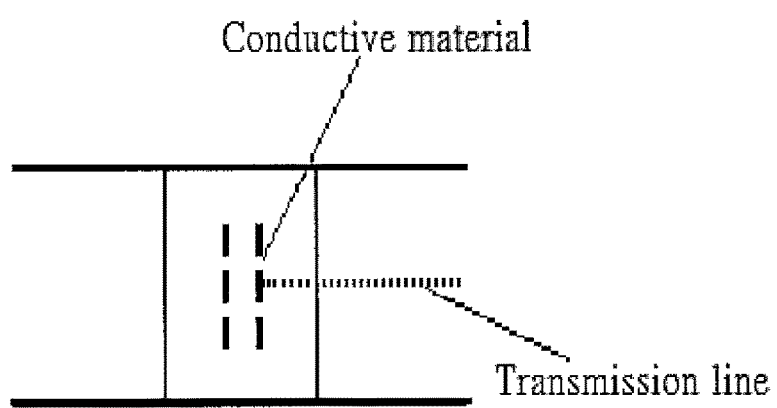
FIGS. 23A to 23D are schematic diagrams of two different buttons of the invention.
Figure 23B:
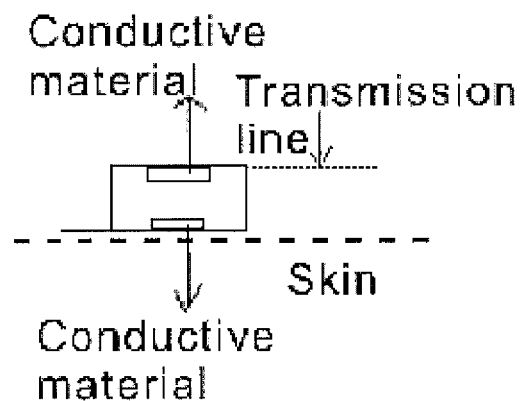
Figure 23C:
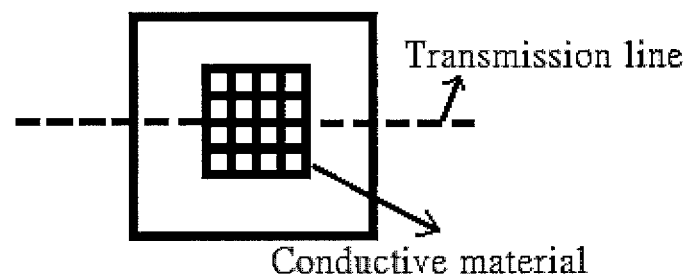
Figure 23D:
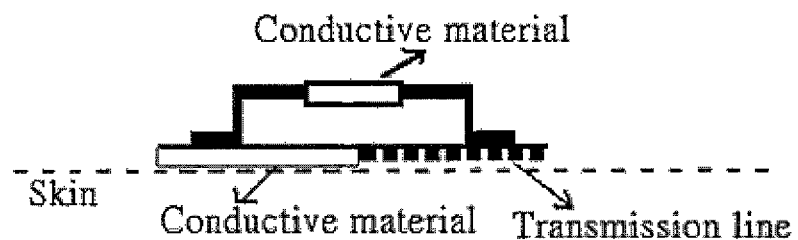
Figure 24A:
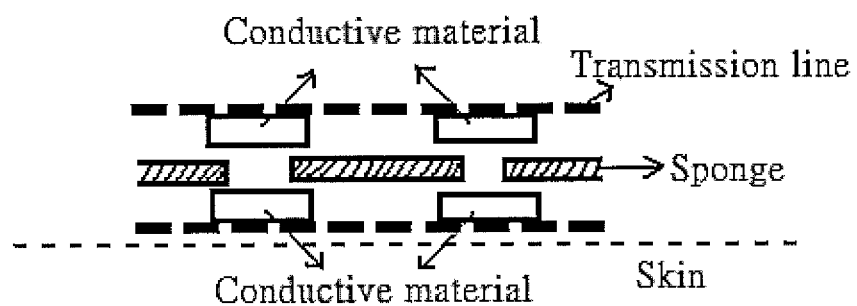
FIGS. 24A to 24B are schematic diagrams of buttons with sponge of the invention, wherein electrodes are above the sponge.
Figure 24B:
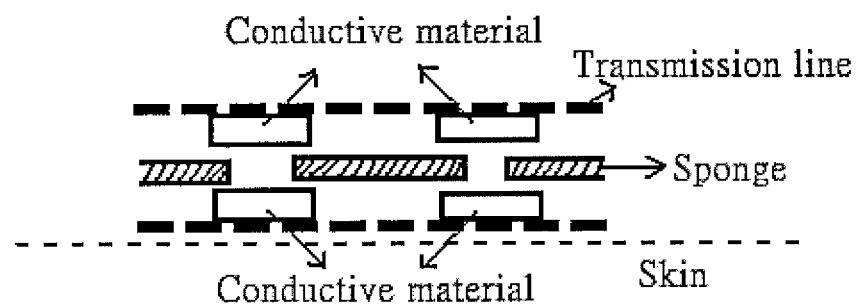
Figure 24C:
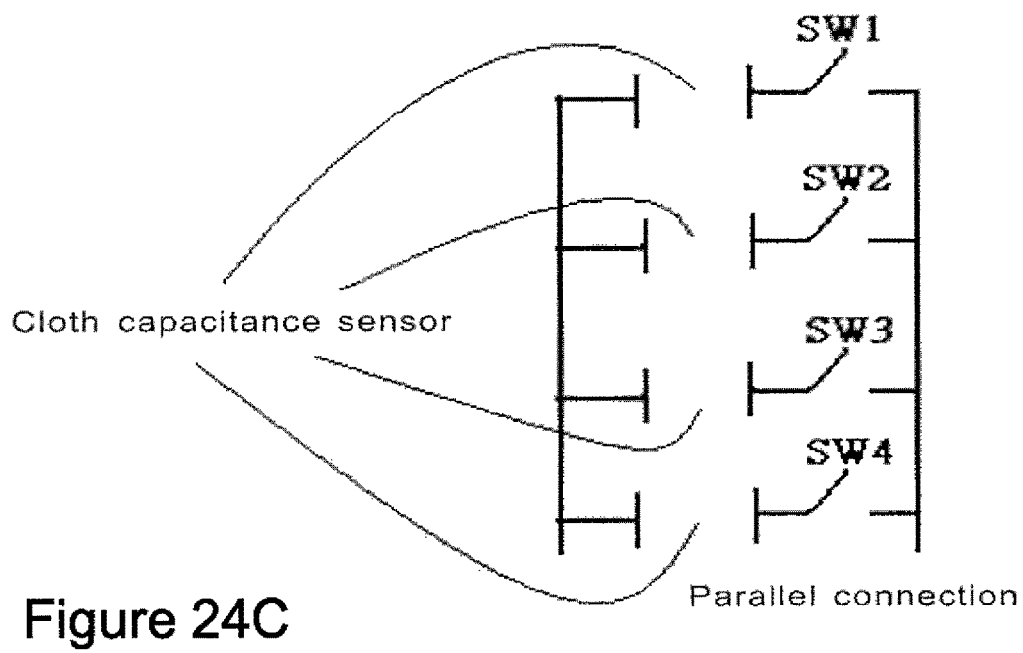
FIGS. 24C to 24D are circuit diagrams of the cloth capacitive sensor connected in series or in parallel with buttons of the invention.
Figure 24D:
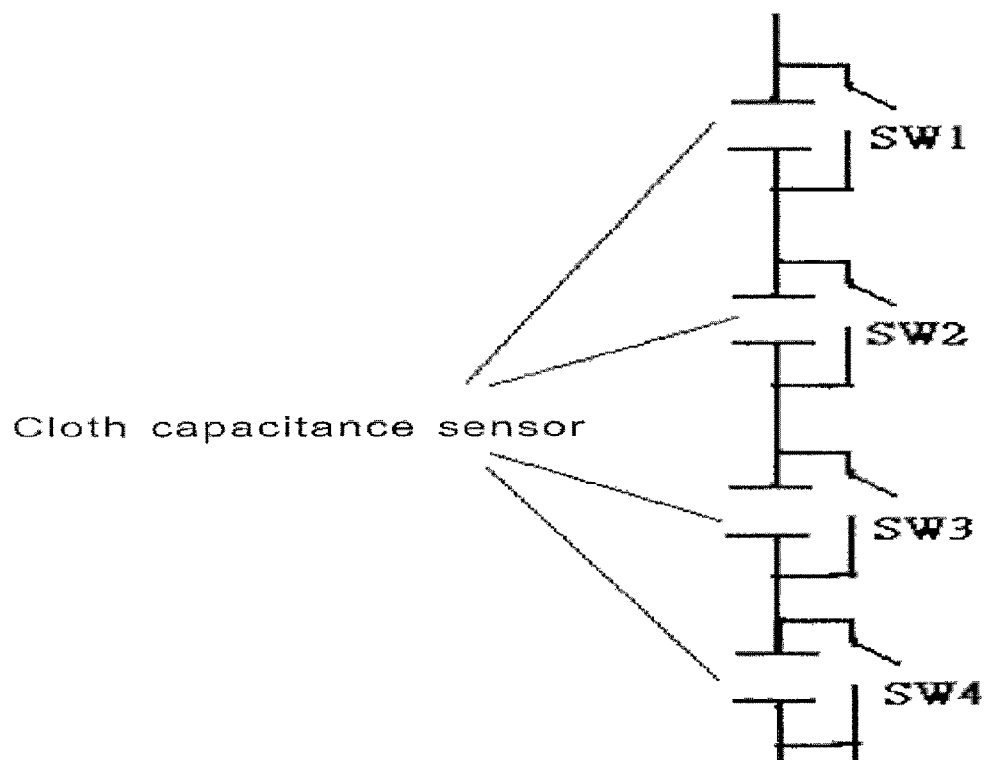
Figure 24E:
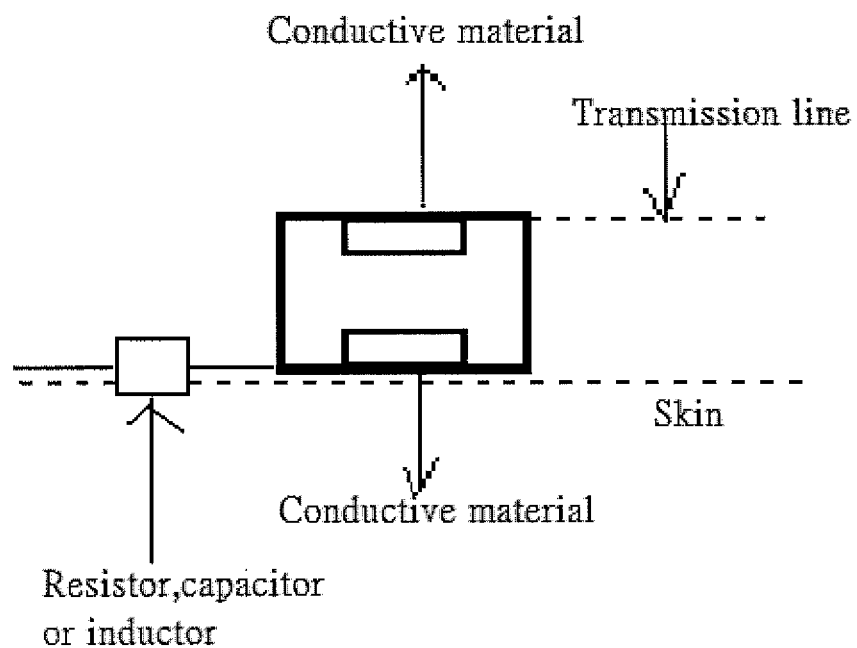
FIGS. 24E to 24I are schematic diagrams of five different buttons of the invention.
Figure 24F:
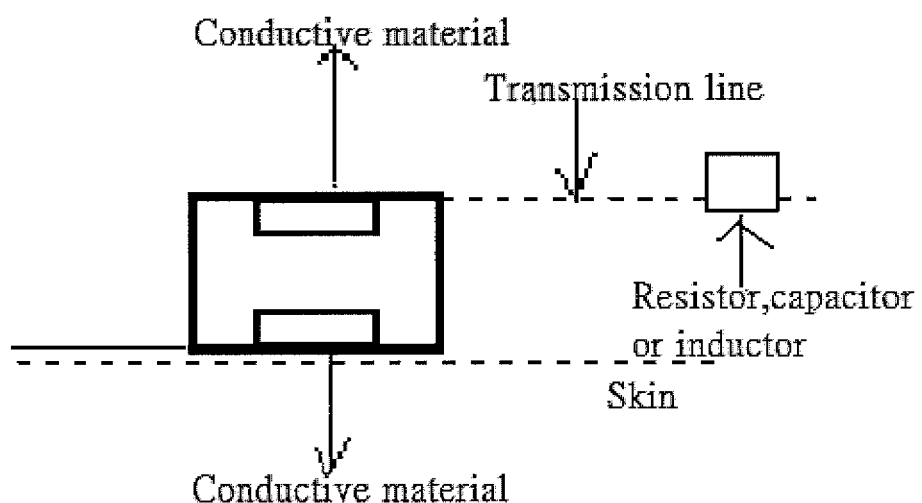
Figure 24G:
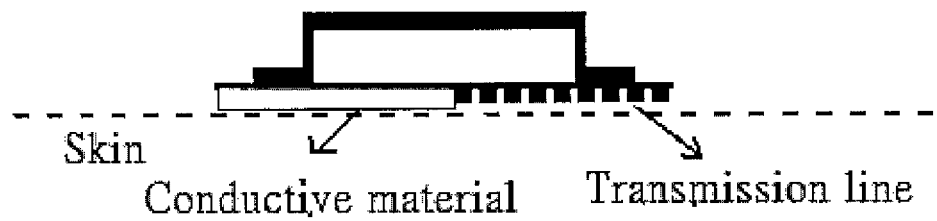

The switches are arranged on specific positions shown as FIGS. 23A to 23D which are schematic diagrams of two different buttons. For example, under a certain pressure, such as 10 kg, the capacitance variation of the cloth capacitive sensor on the buttons contacted with the human body is sensed. There is signal output under pressure of below 10 kg. Conductive fiber is arranged at the bottom of the buttons shown as FIGS. 23A to 23D in which conductive materials are arranged on the buttons up and down. In addition, in the condition that the conductive material not contacted with the human body is connected with the transmission line, the FIG. 23A is a plan view diagram and the FIG. 23B is a side view diagram. FIGS. 23C and 23D are in the other form. The FIG. 23C is a plan view diagram and the FIG. 23D is a side view diagram. Under effect of external forces, the buttons are downward so that the conductive materials contacted with the body have capacitance change. In addition, if the conductive materials contacted with the body are removed, the conductive materials above the button are contacted with the body so as to change the capacitance, which means the buttons are in the cloth capacitive sensors. In addition, FIGS. 24A and 24B are schematic diagrams of more than one button. FIGS. 24C to 24D are circuit diagrams where the cloth capacitive sensors connected in series or in parallel with the buttons, thereby saving wires to a great extent. Two cloth capacitive sensors are connected in series or in parallel with one button. In addition, a resistor R, a capacitor C or an inductor L can be further connected in series with each cloth capacitive sensor shown as FIGS. 24E and 24F to change the signal range of its frequency, voltage or current so as to analyze physiological signals or posture changes at different positions. We not only know the physiological signals or posture changes but also understand where the signal is generated from the body.

Figure 24H:
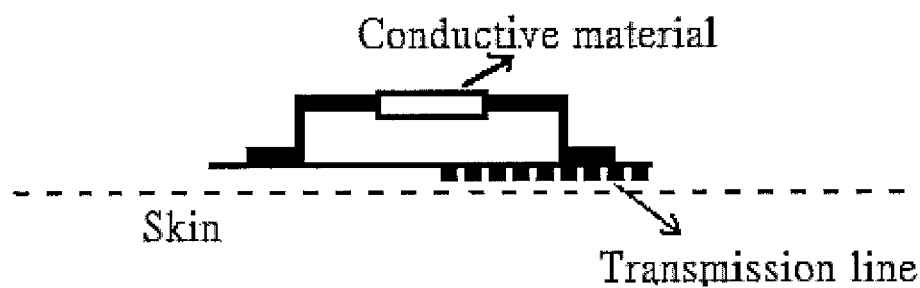
Figure 24I:
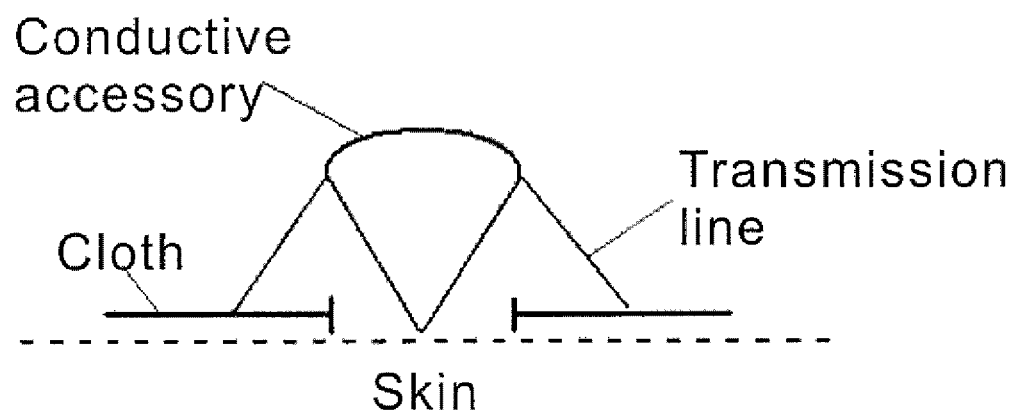

The sponge in the FIG. 24A is placed between the transmission line and the conductive cloth. Under external forces, the upper and lower conductive cloth will be pressed on and under no external forces, the upper and lower conductive cloth is recovered to off state. The conductive cloth itself serves as the conductive area. That is to say, the button itself is not only a button, but also a conductive area to sense change on capacitance. The FIG. 24B is only provided with upper conductive cloth. At the same, the upper conductive cloth presses the sponge to be contacted with the human body to cause obvious change in capacitance. So, the button itself is the cloth capacitive sensor. FIGS. 24A to 24B are schematic diagrams of buttons with sponge and with electrodes on the sponge. In addition, the button is not necessarily connected with the conductive area or is separated from the conductive area. Shown as FIG. 24Q there is no conductive material above the button. Or shown as FIG. 24H, the conductive material contacted with the human body is removed and the conductive material above the button is contacted with the human body to cause change on capacitance, that is to say, the button itself is not only taken as a button switch, but also serves as the conductive area to sense the change on capacitance. Further shown as FIG. 24I, the cloth is provided with a through hole and a conductive accessory. The conductive material on the accessory is contacted with the body to generate change in capacitance.

The switch can be a key switch, a crack switch or a multistage switch. The switch further can be an analogue switch or a digital switch. In addition, the button can be an electronic switch of PCT/CN2005/001520. The cloth in PCT/CN2008/001571 capable of forming electronic element or cloth in PCT/CN2008/001570 with separated induction area can be digital pull or pressure sensors with a predetermined critical value to start another biosensor connected such as body temperature sensor, blood pressure sensor, ECG, EMG, blood oxygen sensor, EEG, blood sugar sensor, sweat sensor, posture sensor or biosensor or to close the primary article being sensed. When it is used as switch and placed in article contacted with the body, it can be combined with electrodes. As each switch has a critical value of external force, when the external force is greater than the critical value, the physiological signals can enter the signal process through the electric sensor. Certainly, the cloth capacitive sensors are unnecessarily connected with a biosensor when used to measure electrocardiogram, electromyogram, brainwave, body fat or sweat because the cloth capacitive sensors are electrodes.

The technology can be further used to measure heartbeat and pulsation, that is to say, when the testee sits down or lies down, the front electrode on the left chest can sensor the frequency change caused by heartbeat. Although the change is not great, it can be sensed. And similarly, the pulsation can be sensed. The electrode is placed on abdomen to distinguish heartbeat, breathing, coughing and judge the movement of the abdomen. The posture changes are not limited in hands and feet and neck, and changes at other positions can be sensed similarly.

Embodiment XI

Figure 25A:
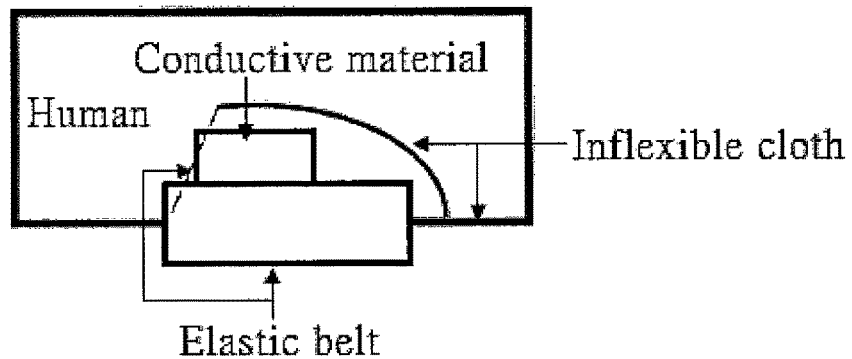
FIGS. 25A to 25B are schematic diagrams of horizontal and vertical displacement sensor of the invention.
Figure 25B:
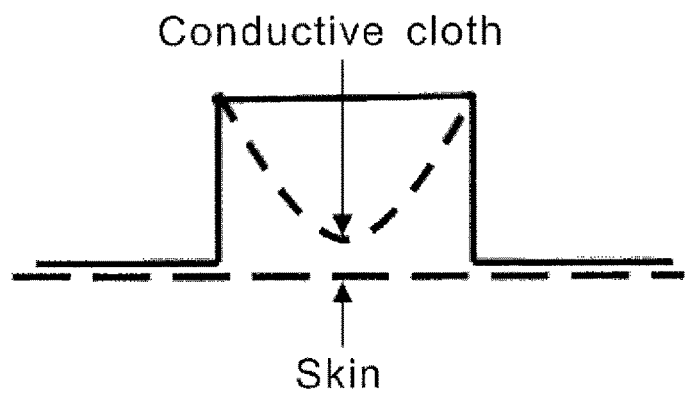

At the same time, the cloth capacitive sensor can be used to sense displacement. For example, the sensing cloth electrode is sewed on elastic cloth by elastic cloth such as an elastic band and the conductive cloth is further shielded by inflexible cloth. Another piece of inflexible cloth is connected with the elastic cloth. One end of the elastic cloth is sewed on the inflexible cloth while the other end is fixed on the inflexible cloth at the other end by the elastic cloth shown as FIG. 25A which is a sectional diagram. Shown as table 6-1, the area of the sensor touching the belly changes along with the change of waistline of the belly during breathing and after exhalation, the wasteline is 82.5 cm and the area pulled of the sensor is minimum and the frequency is 62 KHz maximally. After inhalation, the waistline is 86 cm and the area pulled of the sensor is maximum, the area contacted with the body is maximum and the minimum frequency is 24 KHz. Therefore, the method can be used to sense horizontal displacement. The conductive material of the vertical displacement sensor shown as FIG. 25B is cone-shaped and changes the contact area by vertical displacement, which means that the cloth capacitive sensor serves as the displacement sensor. With above characteristics, the cloth capacitive sensor exposes more areas of conductive materials when strained and is in stretch-recovery when not strained or exposes more areas of conductive materials when pressed and is in pressure-recovery when not pressed.

TABLE 6-1

| Waistline | | | | | | | |
|---|---|---|---|---|---|---|---|
| 82.5 | 83 | 83.5 | 84 | 84.5 | 85 | 85.5 | 86 cm |
| Frequency 62 | 51 | 45 | 41 | 37 | 33 | 28 | 24 KHz |

The technology is used to measure the physiological information of posture changes of the body and can be further provided with an accelerometer or a gyroscope, an inclinometer and a magnetometer etc. to assist sensing for accuracy. We sense continuously for the capacitive sensors are placed in articles contacted with the human body for a long time, such as socks, protective clothing, slippers, insoles, shoes, safety belts, trousers, clothes, hats, masks and gloves etc. The capacitive sensors can be further used for artificial products such as artificial limbs, artificial eyes and artificial ears etc. Thus, behaviors of the testee can be sensed, such as finger movement, head rotation, heat applied by external forces or not, stooping, crouching, hand swinging, foot bending, and leg movement etc so as to obtain behavior movement of the human body. The plurality of capacitive sensors at the sole can measure the walking speed of feet, acceleration and walking distance of the testee. In addition, it can be used to know whether the human body is applied by external forces or not. For example, the capacitive sensors are arranged on the protective clothing and shoes to measure pressure, tension, pull and strain at different positions. And it can be further used to movement such as protective clothing for taekwondo or safety belts, wherein the safety belts are provided with the capacitive sensors to measure whether the testee belts up or not during driving, and know whether the human body is applied by external forces.

Similarly, we can use the capacitive sensors to measure humidity and body temperature of human body. In addition, the capacitive sensors at different parts of the human body can be used to measure pressure, tension, pull and strain at different parts. By cloth capacitive sensors can be used to sense sweat. Wound, sweating, medicine coating, and skin powdering or cosmetics coating can cause change of dielectric constants. The resonance frequencies sensed are different so that the different resonance frequencies can be used to estimate wound recovery of the testee or whether the testee has make-up. The above capacitive sensors can be used for both human and other animals.

In addition, the switch itself can be used as the capacitive sensor which is not necessary contacted with the human body, for example separated by cloth. The result is the same.

When the cotton above the stainless steel cloth is contacted with skin, that is to say the capacitive conductive cloth is not directly contacted with the human body. If it is located at the heel of the socks, the frequency under 5 kg is 102 KHz, that under 10 kg is 100 KHz, that under 20 kg is 94 KHz, that under 30 kg is 90 KHz, that under 40 kg is 86 KHz and that under 50 kg is 85 KHz. The stainless steel conductive cloth can be directly sewed on the socks or on the sole. And the grounded end is sewed near the opening of the socks by the conductive cloth.

Figure 26A:
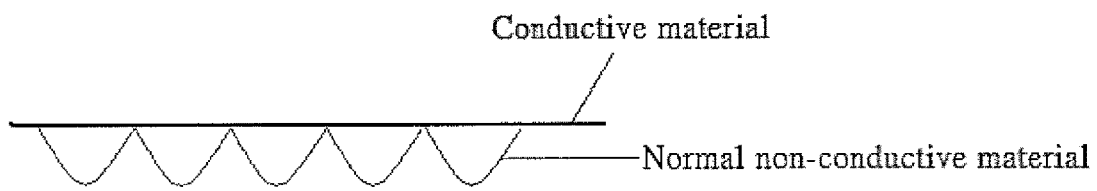
FIGS. 26A to 26B are schematic diagrams of Velcro structure as switch structure of the invention.
Figure 26B:
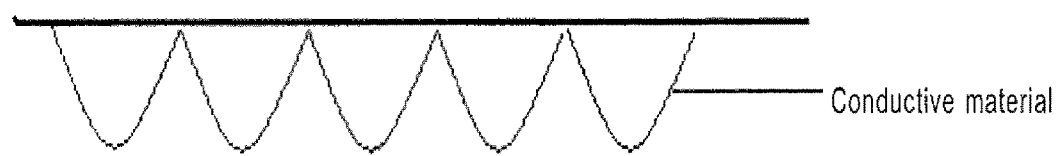
Figure 27:
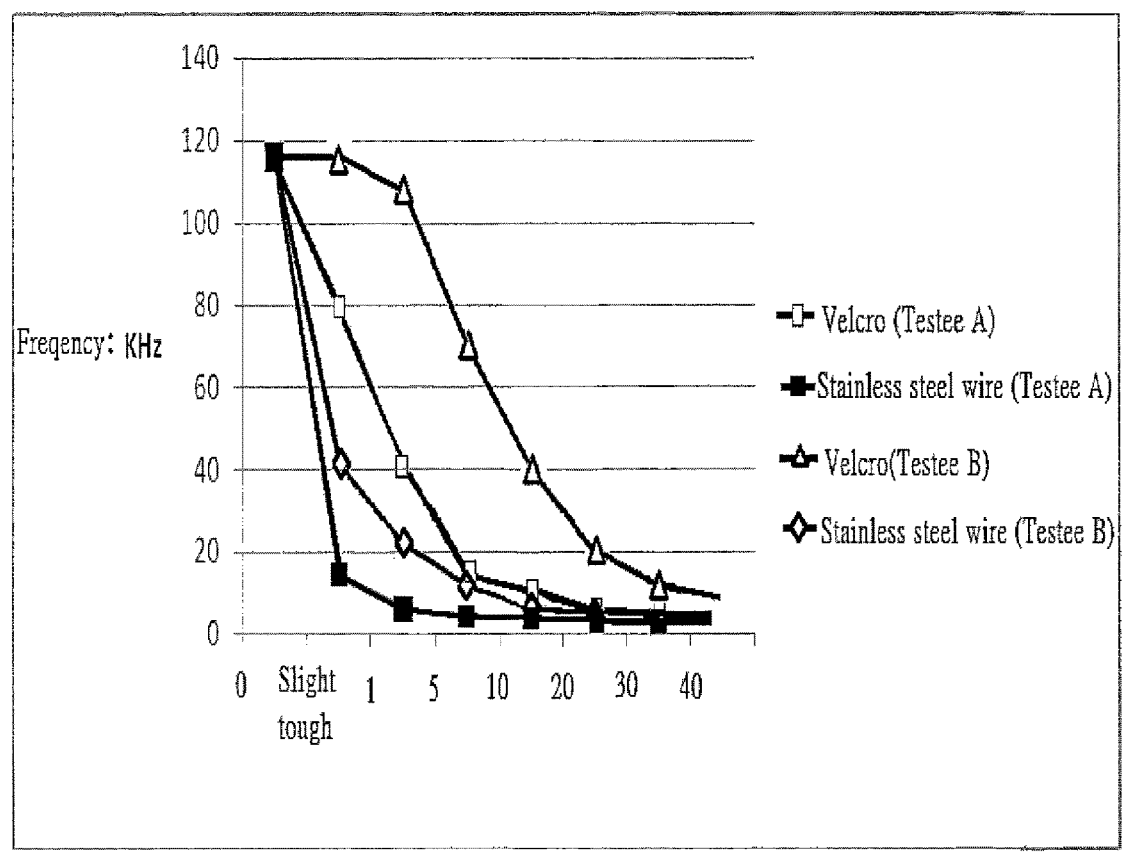
FIG. 27 is a schematic diagram of changes of weight and frequency of the invention when Velcro structure and cotton cloth are sewed with stainless steel lines.

The invention is mainly characterized in that the capacitive sensors are clothes so as to monitor the physiological signals of the human body for a long time. The electrodes for measuring the physiological signal such as electrocardiogram, brainwave and electromyography etc are pressed on the body to a certain degree and the humidity has a certain value so that the capacitive sensors are designed to sense the pressure and humidity and used as electrodes of physiological signal sensors such as ECG, body fat, breathing, humidity, EEG, EMG, which means that the capacitive sensors under a certain pressure or humidity starts to sense the physiological signals or when the physiological are not sensed, the capacitive sensors can measure whether the electrodes are deeply pressed or not or the electrodes are too dry. When basic requirements are not met, the capacitive sensors cannot sense the signals required. The switch structure can be modified to a structure like Velcro Tape, which means that the bottom of the Velcro Tape is provided with the conductive materials (FIG. 26A) or the fiber on the Velcro Tape is the conductive material such as stainless steel or silver fiber (FIG. 26B). Different elasticity and capacitance reactions can be generated by area of the conductive materials. Shown as table 6-2, it is the result of FIG. 27. The stainless steel line is sewed on the bottom surface of the Velcro tape while the other surface is the cotton which is directly sewed with metal line. It can be seen from data that the Velcro Tape has no fiber bumps so that the skin is not directly contacted with the stainless steel line. Therefore, it can be seen from FIG. 27 that the decreasing speed of frequency is milder than the condition that the cotton is directly sewed with metal line. Relatively, usable force range degree of identification can be expanded.

TABLE 6-2

|  | Testee A | | Testee B | |
| --- | --- | --- | --- | --- |
|  | Velcro | Cotton | Velcro | Cotton |
| 0 KG | 116 | 116 | 116 | 116 |
| Slight touch | 80 | 14 | 116 | 41 |
| 1 KG | 41 | 6 | 108 | 22 |
| 5 KG | 14 | 4 | 70 | 12 |
| 10 KG | 10 | 3.5 | 40 | 6 |
| 20 KG | 5.5 | 3 | 20 | 5 |
| 30 KG | 4.5 | 2.8 | 12 | 4.7 |
| 40 KG | 3.5 | 2.7 | 8.6 | 4.7 |
|  | | KHz | | |

When the object is contacted with surface of the human body, an equivalent capacitor is formed on the surface layer of the skin. In the experiment, the electrode sensors are contacted with the skin and the electrodes are pressed so as to apply pressure indirectly to the equivalent capacitor. The equivalent capacitor is applied by pressure, pull, strain or tension so that the capacitance changes and the changes are used to differentiate the capacitance and stress level. For example, whether people wearing a mask breathe with nose, breathe with mouth or speak with mouth can be sensed by the cloth capacitive sensors. Prior to experiment, we assume that the body is a conductor and our experiment is divided into two, one of which is bi-sensor, while the other is a single sensor.

Common architecture of the invention refers to FIG. 1. The articles where the sensors are placed such as clothes, socks, bed sheets, pillows or chairs etc. are contacted directly or indirectly with human body (for example, underwear separates the sensors and the skin). The sensors are arranged at specific positions according to applications and matched with switches according to demand, for example, button switches or crack switches. The technology such as electronic switches in PCT/CN2005/001520 and cloth in PCT/CN2008/001571 capable of forming electronic element or cloth in PCT/CN2008/001570 with separated induction area can be digital tension or pressure sensors with a predetermined critical value to start another biosensor connected to close the primary article being sensed. As each switch has a critical value of external force, when the external force is greater than the critical value, the physiological signals can enter the signal processor. The switches are used to select appropriate part to retrieve the physiological signals according to postures of the human body so as to separate noise caused by incorrect touch effectively and close the power supply of the primary sensor, thereby saving electricity and energy.

In order to increase bonding between the sensors and the human that are contacted, a material can be added between the sensors and the cloth or leather to increase the thickness, such as elastic materials: sponge, silicon, rubber, and spring etc. At the same time, in order to prevent incorrect contact or transmit too many signals at the same time, a switch can be further provided between the sensors and the cloth or leather so as to control start of signal sensing according to pressure or tension.

Physiological signals are associated with pressure or tension between human body and sensors. When the human body and sensors are not contacted, there is no signal; when the human body and sensors are in poor contact, the signal is not better. In the invention, the button switches or the crack switches are connected in series or in parallel with sensors. When the pressure is enough, the physiological signals are transferred to the circuit so that many sensors share one transmission line so as to prevent unnecessary physiological signals from interfering required signals that are actually recorded, thereby, reducing the number of transmission lines and making the user more comfortable. And when the user changes the posture, there are still sensors pressed to obtain the physiological signals. For example, a button switch at the back is connected in series with the sensors. When the user lies on his back and the back presses the mattress, the physiological signals obtained by the sensors are transferred to the circuit. In another example, a crack switch at the kneecap is connected in parallel with the sensors. When the user bends the knee, the crack switch is pulled open by tension and the crack switch signal changes from "ON" to "OFF". Trousers will be adjacent to knee-joint by tension and the cloth capacitive sensors connected with the crack switch change by tension and the sensor at the position obtains the physiological signals when the change in capacitance is measured. When the user straights the legs, trousers will be out of tension and will not be adjacent to the knee-joint so that the sensors cannot obtain the physiological signals.

In brief, the system for generating physiological signals by using a cloth capacitive sensor in the invention comprises at least a piece of cloth and an oscillating circuit. A capacitor is formed between the conductive cloth and the human body. When pressure, pull, or strain are applied between the human body and the cloth, which enables to change the capacitance or change the dielectric constant between the human body and the cloth so that the capacitance changes, the oscillating circuit is used to send signals. The system receives the change in capacitance between the conductive cloth and the human body; the change is represented by frequency, period, voltage or current change which is used to analyze at least one piece of information of physiological and posture changes of human body, medium change between the human body and the cloth or information of force applied. Furthermore, a switch is connected with the conductive cloth or the switch itself is the capacitive sensor. Different frequency, voltage or current change curves can be measured in different physiological statuses in the system. The system which can be used to sense posture change can be used to measure other physiological information such as heartbeat, body temperature, humidity and breathing. In addition, the conductive cloth is not directly contacted with the human body, and a material is set between the conductive cloth and the human body, such as a layer of cloth, rubber, plastic (TPU film), waterproof cloth, coating and printing. The capacitive sensors can sense pressure, pull and strain, and serve as biosensors: "electrodes" to sense electrocardiogram, electromyography, breathing and brainwave etc. Therefore, we can obtain different frequency, voltage or current change curves according to different physiological statuses by the capacitive sensors, for example we can sense gait stability of human body according to signal changes generated by two feet sensors. Furthermore, for example, when pressure between the conductive cloth of the capacitive sensors and the human body reaches 1 kg, value of temperature sensor (thermistor) is started to read. That is to say, the conductive cloth serves as a pressure sensor, and when the critical value is achieved, signals of other physiological sensors in adjacent positions are started to read. Furthermore, for example, the conductive cloth itself can be used as electrode, and starts to measure electrocardiogram, electromyography, brainwave or breathing of two or three pieces of conductive cloth when the pressure reaches 1 kg. Or the conductive cloth can be used as treatment electrodes to generate TENS, heat or reduce temperature. The pressure above can be pull, tension and strain.

The above contents are only better embodiments of the invention and do not limit the invention in any forms. Although the invention is disclosed with the better embodiments above, the contents are not to limit the invention. Technical personnel familiar with the profession can work out equivalent embodiments with some changes or modifications as equivalent changes according to the method and technical contents disclosed within the range of the technical solution of the invention. For any contents within the technical solution of the invention, any simple amendments, equivalent changes or modifications for the above embodiments according to the technical essence of the invention are still within the range of technical solution of the invention.

The invention claimed is:

1. A system for generating physiological signals using a cloth capacitive sensor, comprising
    at least a piece of cloth;
    at least one conductive area arranged on the cloth
    a signal circuit;
    a capacitive sensor formed between the at least one conductive area and the skin of body, wherein the at least one conductive area is in direct contact with the skin of body;
    and
    a resistor R, a capacitor C, an inductor L, an operational amplifier, a diode, a Schmitt trigger, CMOS, a transistor, or an IC that forms a charge or discharge circuit, connected, in series or in parallel, with the cloth capacitive sensor to change a signal range of frequency, cycle, voltage or current;
    wherein when a pressure, stretching force, torsion, or tensile force is applied between the body and the cloth, or when a dielectric constant between the body and the cloth changes, the capacitance changes, the signal circuit sends a signal that comprises the change in capacitance between the at least one conductive area arranged on the cloth and the body to the system;
    wherein the change is represented by a frequency, cycle, voltage or current change, which is used to determine physiological change, posture change, medium change between the body and the cloth, gait analysis, and or at least one of the applied pressure, the stretching force, the torsion, or the tensile force.

2. The system for generating physiological signals using the cloth capacitive sensor according to claim 1, wherein a material is set between the at least one conductive area and the skin.

3. The system for generating physiological signals using the cloth capacitive sensor according to claim 1, wherein the physiological change information is selected from a group consisting of: breathing, swallowing, coughing, sweating, heartbeat, pulsation and temperature.

4. The system for generating physiological signals using the cloth capacitive sensor according to claim 1, wherein the conductive cloth is provided on clothing, hats, pants, masks, socks, shoes, bed sheets, pillows, gloves, steering wheels, crutches, tablecloth, chairs, carpets, protective clothing, slippers, insoles, safety belts, hats, or artificial products including artificial limbs, artificial eyes and artificial ears.

5. The system for generating physiological signals using the cloth capacitive sensor according to claim 1, wherein sweat, wound, sweating, medicine coating or makeup is detected through a change of dielectric constants caused by the change in capacitance between the at least one conductive area and the skin.

6. The system for generating physiological signals using the cloth capacitive sensor according to claim 1, wherein the change in capacitance between the conductive cloth and the skin further determines one from a group consisting of: angle, angular speed or angular acceleration of joints.

7. The system for generating physiological signals using the cloth capacitive sensor according to claim 1, wherein the change in capacitance between the conductive cloth and the skin further determines one from a group consisting of: position, displacement, speed, acceleration, center of mass change, center of mass speed, center of mass acceleration and travelling distance.

8. The system for generating physiological signals using the cloth capacitive sensor according to claim 1, wherein the at least one conductive area is made by a different conductive material or by the same conductive materials having differing size areas.

9. The system for generating physiological signals using the cloth capacitive sensor according to claim 1, wherein the system further comprises a reference conductive area, the reference conductive area is grounded, wherein the signal circuit also sends a signal that comprises the change in capacitance between the reference conductive area and the body to the system.

10. The system for generating physiological signals using the cloth capacitive sensor according to claim 1, wherein sleep actigraphy of a human body can be detected by the cloth capacitive sensor.

11. The system for generating physiological signals using the cloth capacitive sensor according to claim 1, wherein
    an elastic material is coated on the cloth;
    the cloth comprises an elastic material; or
    a material of the conductive area is conductive wires or conductive yarns.

12. A method for generating physiological signals using a cloth capacitive sensor, comprising:

providing a system for generating physiological signals, wherein the system comprises
at least a piece of cloth;
at least one conductive area arranged on the cloth
a signal circuit;
a capacitive sensor formed between the at least one conductive area and the skin of body, wherein the at least one conductive area is in direct contact with the skin of body;
a resistor R, a capacitor C, an inductor L, an operational amplifier, a diode, a Schmitt trigger, CMOS, a transistor, or an IC that forms a charge or discharge circuit, connected, in series or in parallel, with the cloth capacitive sensor to change a signal range of frequency, cycle, voltage or current;
wherein when pressure, stretching force, torsion, or tensile force, is applied between the body and the cloth, or when a dielectric constant between the body and the cloth changes, the capacitance changes, the signal circuit sends a signal that comprises the change in capacitance between the at least one conductive area arranged on the cloth and the body to the system;
measuring the change in the capacitance, wherein the change is represented by frequency, cycle, voltage or current change; and
determining, from the change in capacitance, physiological change, posture change, medium change between the body and the cloth, gait analysis, or at least one of the applied pressure, the stretching force, the torsion, or the tensile force.

13. The method for generating physiological signals using the cloth capacitive sensor according to claim 12, wherein the change represented by frequency, cycle, voltage, or current change is used to further determine at least one selected from a group consisting of: gait analysis, gait stability, fall, sleep actigraphy or displacement, or sleep.

14. The method for generating physiological signals using the cloth capacitive sensor according to claim 12, further measuring a change in capacitance between a reference conductive area and the body, wherein the reference conductive area is grounded.

15. The method for generating physiological signals using the cloth capacitive sensor according to claim 12, wherein the at least one conductive area comprises an electrode for monitoring heartbeat, breathing, brainwave, electromyography (EMG) or electrocardiogram (ECG), body fat or sweat, or for generating transcutaneous electrical nerve stimulation (TENS), heat or reduce temperature.

16. The method for generating physiological signals using the cloth capacitive sensor according to claim 12, wherein sleep actigraphy of a human body can be detected by the cloth capacitive sensor.

17. The method for generating physiological signals using the cloth capacitive sensor according to claim 12, wherein
an elastic material is coated on the cloth;
the cloth comprises an elastic material; or
a material of the conductive area is conductive wires or conductive yarns.

18. The method for generating physiological signals using the cloth capacitive sensor according to claim 12, wherein the physiological change information is selected from a group consisting of: breathing, swallowing, coughing, sweating, heartbeat, pulsation and temperature.

19. The method for generating physiological signals using the cloth capacitive sensor according to claim 12, wherein the at least one conductive area comprises an electrode for monitoring heartbeat, breathing, brainwave, electromyography (EMG) or electrocardiogram (ECG), body fat or sweat, or for generating transcutaneous electrical nerve stimulation (TENS), heat or reduce temperature.

20. The method for generating physiological signals using the cloth capacitive sensor according to claim 12, wherein the conductive cloth is provided on clothing, hats, masks, socks, shoes, bed sheets, pillows, gloves, steering wheels, crutches, tablecloth, chairs, carpets, protective clothing, slippers, insoles, safety belts, hats, or artificial products including artificial limbs, artificial eyes and artificial ears.

21. The method for generating physiological signals using the cloth capacitive sensor according to claim 12, wherein sweat, wound, sweating, medicine coating or makeup is detected through a change of dielectric constants caused by the change in capacitance between the conductive cloth and the skin.

22. The method for generating physiological signals using the cloth capacitive sensor according to claim 12, wherein the change in capacitance between the conductive cloth and the skin further determines one from a group consisting of: angle, angular speed or angular acceleration of joints.

23. The method for generating physiological signals using the cloth capacitive sensor according to claim 12, wherein the change in capacitance between the conductive cloth and the skin further determines one from a group consisting of: position, displacement, speed, acceleration, center of mass change, center of mass speed, center of mass acceleration and travelling distance.

24. The method for generating physiological signals using the cloth capacitive sensor according to claim 12, wherein the at least one conductive area is made by a different conductive material or by the same conductive materials having differing size areas.

25. The method for generating physiological signals using the cloth capacitive sensor according to claim 12, wherein a material is set between the at least one conductive area and the skin.

* * * * *